United States Patent
Jang et al.

(10) Patent No.: US 10,024,785 B2
(45) Date of Patent: Jul. 17, 2018

(54) SOLID HEMOGLOBIN-POLYMER BIOPHOTONIC PHANTOMS AND THEIR USE

(71) Applicants: The United States of America, as represented by the Secretary, Department of Health and Human Services, Washington, DC (US); University of Maryland, College Park, College Park, MD (US)

(72) Inventors: Hyounguk Jang, Silver Spring, MD (US); Jianting Wang, Silver Spring, MD (US); Yu Chen, Rockville, MD (US); Thomas Joshua Pfefer, Chevy Chase, MD (US)

(73) Assignees: The United States of America, as represented by the Secretary, Department of Health and Human Services, Washington, DC (US); University of Maryland, College Park, College Park, MD (US)

( * ) Notice: Subject to any disclaimer, the term of this patent is extended or adjusted under 35 U.S.C. 154(b) by 208 days.

(21) Appl. No.: 15/187,727

(22) Filed: Jun. 20, 2016

(65) Prior Publication Data
US 2016/0370285 A1 Dec. 22, 2016

Related U.S. Application Data

(60) Provisional application No. 62/182,275, filed on Jun. 19, 2015.

(51) Int. Cl.
*C08J 3/00* (2006.01)
*C08L 83/04* (2006.01)
(Continued)

(52) U.S. Cl.
CPC ............ *G01N 21/278* (2013.01); *C08J 3/005* (2013.01); *C08L 83/04* (2013.01); *G01N 21/359* (2013.01);
(Continued)

(58) Field of Classification Search
CPC .......... A61B 2560/0233; A61B 5/0075; A61B 5/0095; C08J 2383/04; C08J 2489/00;
(Continued)

(56) References Cited

U.S. PATENT DOCUMENTS

2010/0046902 A1\* 2/2010 Kaplan ................. B29D 11/00
385/129

OTHER PUBLICATIONS

Pogue, et al. "Review of tissue simulating phantoms for optical spectroscopy, imaging and dosimetry." Journal of Biomedical Optics 11, No. 4 (2006): 041102-041102. (Year: 2006).\*
(Continued)

*Primary Examiner* — Jennifer Wecker
(74) *Attorney, Agent, or Firm* — Klarquist Sparkman, LLP

(57) ABSTRACT

Novel biophotonic phantoms are provided herein that can accurately mimic the optical properties of living tissue. The disclosed biophotonic phantoms comprise hemoglobin (Hb) in a native conformation that is distributed in a solid polymer matrix. Methods of producing the disclosed biophotonic phantoms are also provided. The biophotonic phantoms can be used, for example, to calibrate or test an optical imaging system, such as a near infrared spectroscopy imaging system.

27 Claims, 12 Drawing Sheets

(51) Int. Cl.
| | |
|---|---|
| G01N 33/49 | (2006.01) |
| G01N 21/27 | (2006.01) |
| G01N 21/359 | (2014.01) |
| G01N 21/65 | (2006.01) |
| A61B 5/00 | (2006.01) |
| G01N 21/64 | (2006.01) |

(52) U.S. Cl.
CPC .............. *G01N 21/65* (2013.01); *G01N 33/49* (2013.01); *A61B 5/0075* (2013.01); *A61B 5/0095* (2013.01); *A61B 2560/0233* (2013.01); *C08J 2383/04* (2013.01); *C08J 2489/00* (2013.01); *C08L 2203/02* (2013.01); *C08L 2205/22* (2013.01); *G01N 2021/6417* (2013.01)

(58) Field of Classification Search
CPC ... C08J 3/005; C08L 2203/02; C08L 2205/22; C08L 83/04; G01N 2021/6417; G01N 21/278; G01N 21/359; G01N 21/65; G01N 33/49
See application file for complete search history.

(56) References Cited

OTHER PUBLICATIONS

Ayers, et al. "Fabrication and characterization of silicone-based tissue phantoms with tunable optical properties in the visible and near infrared domain." Biomedical Optics (BiOS) 2008, pp. 687007-687007. International Society for Optics and Photonics, 2008. (Year: 2008).*

Akl, et al. "Optimizing probe design for an implantable perfusion and oxygenation sensor." *Biomedical Optics Express* 2, No. 8 (2011): 2096-2109.

Andersson-Engels, et al. "In vivo fluorescence imaging for tissue diagnostics." *Physics in Medicine and Biology* 42, No. 5 (1997): 815.

Ayers, et al. "Fabrication and characterization of silicone-based tissue phantoms with tunable optical properties in the visible and near infrared domain." *Biomedical Optics (BiOS)* 2008, pp. 687007-687007. International Society for Optics and Photonics, 2008.

Bays, et al. "Three-dimensional optical phantom and its application in photodynamic therapy." *Lasers in Surgery and Medicine* 21, No. 3 (1997): 227-234.

Beyer, et al. "A combined PET/CT scanner for clinical oncology." *J Nucl Med* 41 (2000): 1369-1379.

Bosschaart, et al. "A literature review and novel theoretical approach on the optical properties of whole blood." *Lasers in Medical Science* 29, No. 2 (2014): 453-479.

Brooksby, et at. "Spectral priors improve near-infrared diffuse tomographyaphy more than spatial priors." *Optics Letters* 30, No. 15 (2005): 1968-1970.

Bydlon, et al. "Chromophore based analyses of steady-state diffuse reflectance spectroscopy: current status and perspectives for clinical adoption." *Journal of Biophotonics* 8, No. 1-2 (2015): 9-24.

Cai, et al. "Raman, mid-infrared, near-infrared and ultraviolet—visible spectroscopy of PDMS silicone rubber for characterization of polymer optical waveguide materials." *Journal of Molecular Structure* 976, No. 1 (2010): 274-281.

Cuccia, et al. "Modulated imaging: quantitative analysis and tomography of turbid media the spatial-frequency domain." *Optics Letters* 30, No. 11 (2005): 1354-1356.

Drezek, et al. "Optical imaging of the cervix."*Cancer* 98, No. S9 (2003): 2015-2027.

Durkin, et al. "Optically dilute, absorbing, and turbid phantoms for fluorescence spectroscopy of homogeneous and inhomogeneous samples." *Applied Spectroscopy* 47, No. 12 (1993): 2114-2121.

Fercher, et al. "Optical coherence tomography-principles and applications." *Reports on Progress in Physics* 66, No. 2 (2003): 239.

Firbank, et al. "A design for a stable and reproducible phantom for use in near infra-red imaging and spectroscopy." *Physics in Medicine and Biology* 38, No. 6 (1993): 847.

Hillman. "Optical brain imaging in vivo: techniques and applications from animal to man." *Journal of Biomedical Optics* 12, No. 5 (2007): 051402-051402.

Hyttel-Sorensen, et at. "Calibration of a prototype NIRS oximeter against two commercial devices on a blood-lipid phantom." *Biomedical Optics Express* 4, No. 9 (2013): 1662-1672.

Jacques. "Opticals properties of biological tissues: a review." *Physics in Medicine and Biology* 58, No. 11 (2013): R37.

Jang, et al. "Oximetry system performance assessment with POM (acetal) phantoms incorporating hemoglobin calibration standards and customized saturation levels." In SPIE BiOS, pp. 931503-931503. International Society for Optics and Photonics, 2015.

Jovicich, et al. "Reliability in multi-site structural MRI studies: effects of gradient non-linearity correction on phantom and human data." *Neuroimage* 30, No. 2 (2006): 436-443.

Kurth, et al. "A dynamic phantom brain model for near-infrared spectroscopy." *Physics in Medicine and Biology* 40, No. 12 (1995): 2079.

Li, et al. "Integrated diffuse optical tomography and photoacoustic tomography: phantom validations." *Biomedical Optics Express* 2, No. 8 (2011): 2348-2353.

Li, et al. "Simultaneous measurement of deep tissue blood flow and oxygenation using noncontact diffuse correlation spectroscopy flow-oximeter." *Scientific Reports* 3 (2013).

Lisensky and Campbell, et al. "Replication and compression of bulk and surface structures with polydirnethylsiloxane elastomer." *Journal of Chemical Education* 76, No. 4 (1999): 537.

Long, et al. "Optofluidic phantom mimicking optical properties of porcine livers." *Biomedical Optics Express* 2, No. 7 (2011): 1877-1892.

Lu, et al. "Medical hyperspectral imaging: a review." *Journal of Biomedical Optics* 19, No. 1 (2014): 010901-010901.

Lualdi, et al. "A phantom with tissue-like optical properties in the visible and near infrared for use in photomedicine." *Lasers in Surgery and Medicine* 28, No. 3 (2001): 237-243.

Machida, et al. "Narrow-band imaging in the diagnosis of colorectal mucosal lesions: a pilot study." *Endoscopy* 36, No. 12 (2004): 1094-1098.

Madsen, et al, "Liquid solid ultrasonically tissue-mimicking materials with very low scatter." *Ultrasound in Medicine & Biology* 24, No. 4 (1998): 535-542.

Movasaghi, et al. "Raman spectroscopy of biological tissues." *Applied Spectroscopy Reviews* 42, No. 5 (2007): 493-541.

Ntziachristos, et al. "Concurrent MRI and diffuse optical tomography of breast after indocyanine green enhancement." *Proceedings of the National Academy of Sciences* 97, No. 6 (2000): 2767-2772.

Pekar, et al. "Fabrication and characterization of phantoms with tissue-like optical properties from 500 to 700nm." *Medical Laser Application* 25, No. 3 (2010): 147-153.

Pogue, et al. "Review of tissue simulating phantoms for optical spectroscopy, imaging and dosimetry." *Journal of Biomedical Optics* 11, No. 4 (2006): 041102-041102.

Prahl, et al. "Determining the optical properties of turbid media by using the adding-doubling method,"*Applied Optics* 32, No. 4 (1993): 559-568.

Pralil. "Tabulated Molar Extinction Coefficient for Hemoglobin in Water." Available online at: http://omlc.org/spectra/hemoglobin/summary.html, last accessed Jun. 17, 2016.

Siesler, et al. *Near-infrared spectroscopy: principles, instruments, applications.* John Wiley & Sons, 2008.

Skala, et at. "Multiphoton microscopy of endogenous fluorescence differentiates normal, precancerous, and cancerous squamous epithelial tissues." *Cancer Research* 65, No. 4 (2005): 1180-1186.

Utzinger, et al. "Reflectance spectroscopy for in vivo characterization of ovarian tissue." *Lasers in Surgery and Medicine* 28, No. 1 (2001): 56-66.

Vandegriff, et al. "The kinetics of O2 release by human red blood cells in the presence of external sodium dithionite." *Journal of Biological Chemistry* 259, No. 20 (1984): 12609-12618.

(56) References Cited

OTHER PUBLICATIONS

Wagniéres, et al. "An optical phantom with tissue-like properties in the visible for use in PDT and fluorescence spectroscopy." *Physics in Medicine and Biology* 42, No. 7 (1997): 1415.

Wang, et al. "Photoacoustic tomography: in vivo imaging from organelles to organs." *Science* 335, No. 6075 (2012): 1458-4462.

Wang, et al. "Three-dimensional printing of tissue phantoms for hiophotonic imaging." *Optics Letters* 39, No. 10 (2014): 3010-3013.

Wolf, et al. "Progress of near-infrared spectroscopy and topography for brain and muscle clinical applications." *Journal of Biomedical Optics* 12, No. 6 (2007): 0621044-062104.

Yang, et al. "Low-cost frequency-domain photon migration instrument for tissue spectroscopy, oximetry, and imaging." *Optical Engineering* 36, No. 5 (1997): 1562-1569.

\* cited by examiner

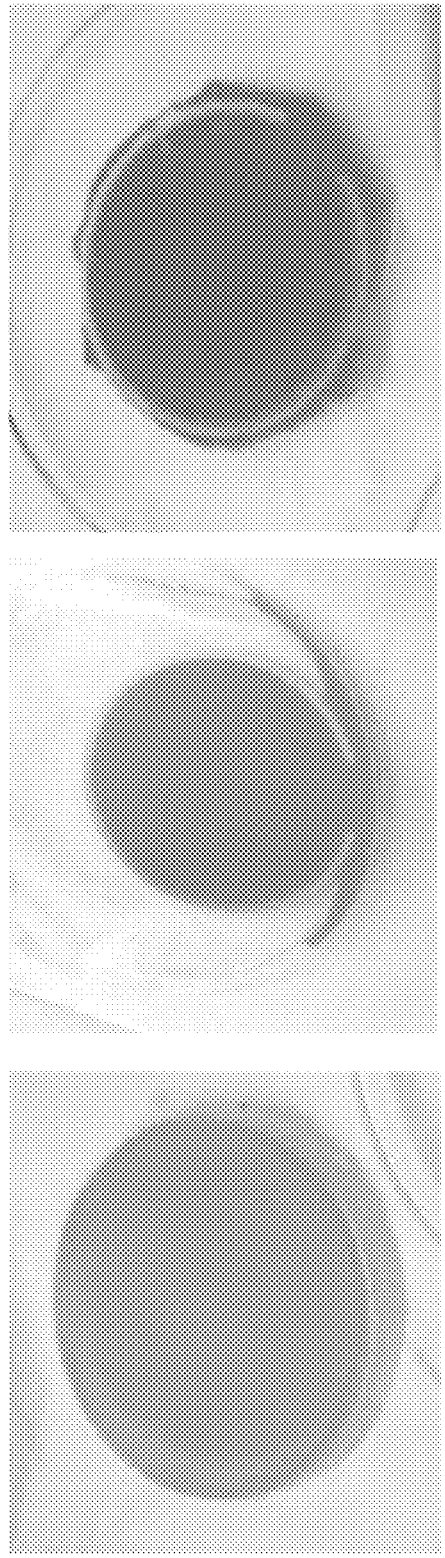

FIG. 10A
FIG. 10B
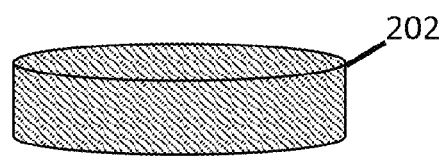
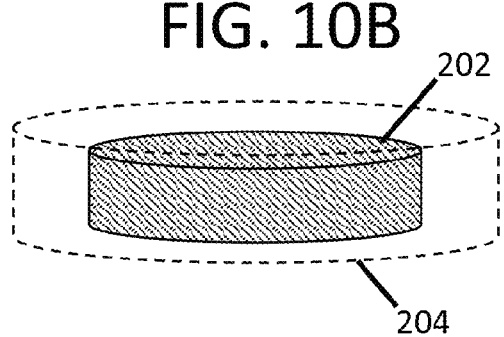
FIG. 10C
FIG. 10D
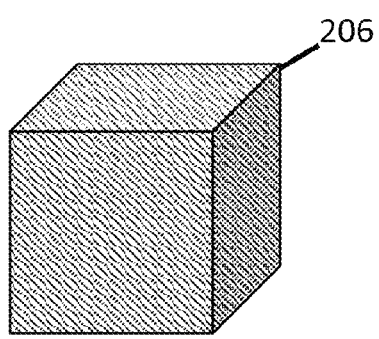
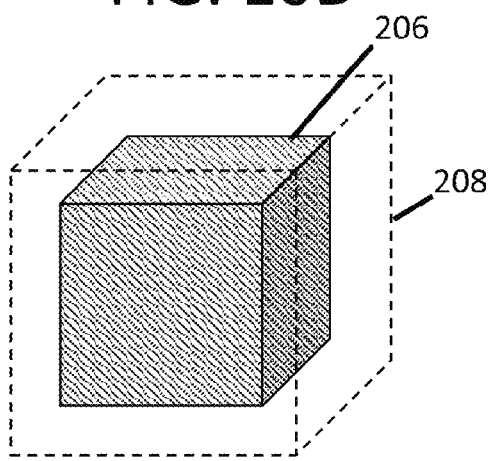

SOLID HEMOGLOBIN-POLYMER BIOPHOTONIC PHANTOMS AND THEIR USE

CROSS REFERENCE TO RELATED APPLICATION

This application claims priority to U.S. Provisional Application No. 62/182,275, which was filed on Jun. 19, 2015, and which is incorporated by reference in its entirety.

FIELD OF THE DISCLOSURE

This relates to biophotonic phantoms that can accurately mimic the optical properties of living tissue and their use, for example, to calibrate and test instrumentation for detecting (such as sensing and imaging) optical properties of a sample.

BACKGROUND

Tissue-simulating phantoms are artificial models with physical properties (e.g., absorption and scattering) similar to biological tissue. They are widely used for performance testing of clinical medical imaging systems (e.g., ultrasound, computed tomography (CT), and magnetic resonance imaging (MRI)). In the field of biophotonics, tissue-simulating phantoms are also used for testing non-imaging diagnostic devices based on spectroscopy and other approaches. The optimal design of a biophotonic phantom depends on the modality and application, and when a higher degree of realism is desired, designs can be customized to individual biological tissue types. The development of phantoms made of specialized materials to mimic biologically-realistic properties has enhanced the quality of these device evaluation tools.

Two relevant characteristics of biophotonic phantoms are the biological relevance of the phantom's optical properties and its long-term stability. Some stable biophotonic phantoms are fabricated from solid polymers and contain artificial dyes that simulate the optical absorption properties of tissue. However, such phantoms do not provide a realistic spectral representation of a ubiquitous biological absorber, hemoglobin (Hb).

SUMMARY

This disclosure provides the first example of a stable biophotonic phantom that provides realistic spectral characteristics of Hb in its oxygenated and deoxygenated forms. The disclosed biophotonic phantoms are stable, have biologically-relevant optical characteristics, and can be used for standardized assessment of optical detection systems.

In some embodiments, a biophotonic phantom is provided that comprises Hb in a native conformation that is distributed in a solid matrix of cured polydimethylsiloxane (PDMS). In several embodiments, the Hb can be homogenously distributed in the solid matrix of cured PDMS. The disclosed biophotonic phantom can comprise an attenuation coefficient and an absorption coefficient across visible and/or near infrared light spectra that remain stable (for example, do not change by more than 10%) for at least two months following construction of the biophotonic phantom.

In some embodiments, the solid matrix of cured PDMS in the biophotonic phantom can comprise from 0.0001% to 5% Hb by weight, such as from 1.0% to 2.5% Hb by weight. The Hb in the solid matrix of cured PDMS can be, for example, oxygenated, partially oxygenated, or deoxygenated.

In some embodiments, the solid matrix of cured PDMS comprising the distributed Hb in the biophotonic phantom can be encased in a shell of polymer material that has low oxygen permeability to inhibit the saturation of the Hb in the phantom. In some embodiments, the solid matrix of cured PDMS comprising the distributed Hb in the biophotonic phantom can be encased in a shell of PDMS that does not comprise Hb. The shell provides a layer of material that inhibits exposure of the Hb in the solid matrix of cured PDMS to air, thereby inhibiting changes in the oxygenation level of the Hb in the phantom.

In some embodiments, the solid matrix of cured PDMS comprising the distributed Hb in the biophotonic phantom can include one or more additives comprising an optical absorber or scatterer to adjust optical properties to mimic the corresponding optical properties of a particular tissue type of interest. Non-limiting examples of the particular tissue type that the phantom can mimic include breast tissue, skin, adipose, brain, kidney, liver, mucosa/epithelium (e.g., oral cavity, esophagus, colon, cervix) and skeletal muscle.

In some embodiments, the solid matrix of cured PDMS comprising distributed Hb can be included in the biophotonic phantom as an inclusion, wherein the inclusion comprises an Hb concentration different from adjacent material in the biophotonic phantom. The inclusion can serve as a target for testing and/or calibrating the performance of an optical detection device (e.g., penetration depth, sensitivity, spectral measurement accuracy, measurement of oxygen saturation, etc.).

The phantom can be shaped as needed for its intended use. In some embodiments, the phantom can have realistic optical and/or acoustic properties and comprise a shape that simulates the morphology of a human organ or tissue or blood vessels, of body parts, or of whole animals, such as a small mammal, for example, a mouse. In some embodiments, the phantom can comprise the shape of a breast, or a portion of a brain. In some embodiments, the phantom can comprise the shape of a cube, cuboid, sphere, ellipsoid, or cylinder.

In some embodiments, one or more filaments, one or more inclusions (such as a solid inclusion or a hollow inclusion filled with that are filled with liquids (e.g., Hb/scatterer/fluorophore solutions), and/or one or more fluid channels, can be embedded in the phantom to provide a series of targets for calibrating or testing the performance characteristics of an optical detection system. In some embodiments, the one or more fluid channels can be filled with a liquid solution comprising optical absorbers and/or scatterers to provide a series of targets for calibrating or testing the performance characteristics of an optical detection system.

In additional embodiments, a method of making a biophotonic phantom is provided. The method comprises mixing Hb that is in a native conformation with uncured PDMS by sonication to form a distributed composition of the Hb and the PDMS. Next, a curing agent is added to the distributed composition of the Hb and PDMS to initiate curing and the composition is formed into the shape of the biophotonic phantom, or a segment thereof, and is allowed to cure. In some embodiments, the sonication step can comprise a duration of from 8-12 hours (such as about 10 hours), wherein episodes of sonication are separated by intervals that permit sufficient heat dissipation to inhibit thermal denaturation of Hb and/or oxidation to methemoglobin (see, e.g., Jarolim et al., Blood 76:10, 1990). In some embodiments, the curing step of the method comprises adding the curing agent to the distributed composition of Hb and PDMS, pouring the composition into an appropriately sized and shaped mold, and incubating the composition in the mold at room temperature for 24 to 48 hours.

In some embodiments, a desaturation agent is added to the composition of Hb and PDMS during the process of making the biophotonic phantom or segment thereof to deoxygenate the Hb in the composition.

Methods of using a disclosed phantom to calibrate or test an optical detection system, such as a Near-Infrared Spectroscopy (NIRS) system or Hyperspectral Reflectance Imaging (HRI) system, are also provided. Optical detection systems including a disclosed phantom are also disclosed.

The foregoing and other features and advantages of this disclosure will become more apparent from the following detailed description of several embodiments which proceeds with reference to the accompanying figures.

BRIEF DESCRIPTION OF THE FIGURES

(FIG. 1A) Main steps in the fabrication process for making the disclosed solid hemoglobin-silicone (PDMS) phantoms. (FIG. 1B) Geometric figure of an embodiment of a disclosed phantom where the solid hemoglobin-silicone (PDMS) phantom (height: 0.3 cm, diameter: 3.8 cm) was encapsulated with a shell of Hb-free PDMS material (height: 1.1 cm, diameter: 6.45 cm). (FIG. 1C) Photo of a cured solid hemoglobin-silicone phantom.

FIGS. 9A-9C are a set of images showing perspective views of embodiments of the Hb-PDMS biophotonic phantoms disclosed herein. The illustrated embodiments are cylindrical non-pigmented skin phantoms incorporating Hb-PDMS composite material, representing normal skin (FIGS. 9A and 9B) and bruised skin with a higher Hb content (FIG. 9C). The phantoms shown in FIGS. 9A and 9B were made with 0.28 mg/g Hb conc., 0.27 g/L Hb, and the phantom shown in FIG. 9C was made with 4.2 mg/g Hb con., 4.05 mg/L Hb.

FIGS. 10A-10D are a set of diagrams showing perspective views of embodiments of the Hb-PDMS biophotonic phantoms disclosed herein that are (FIGS. 10B and 10D) or are not (FIGS. 10A and 10C) encased in a shell of Hb-free PDMS.

DETAILED DESCRIPTION

Figure 1A:
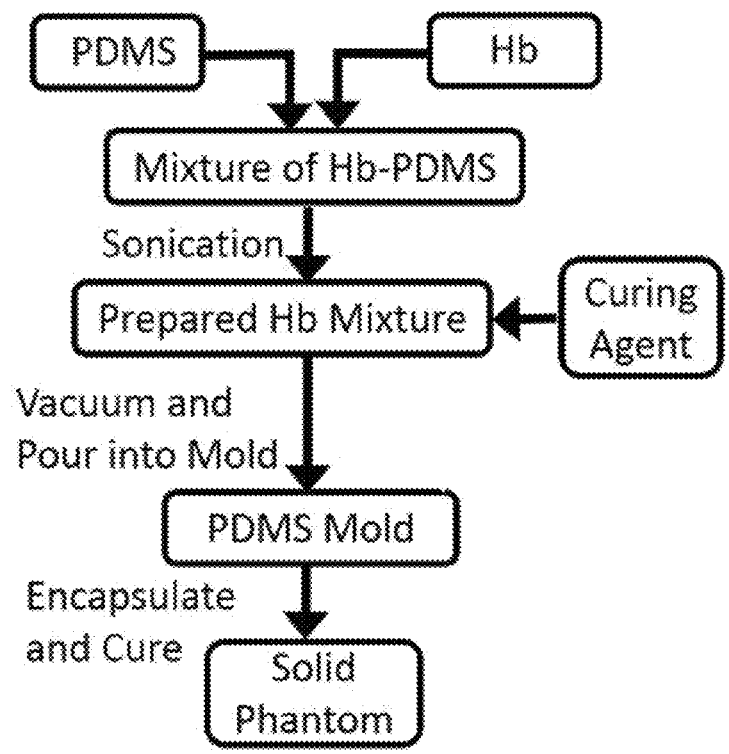
FIGS. 1A-1C illustrate a process of manufacturing an embodiment of the disclosed biophotonic phantoms.

Phantom-based test methods are commonly used in medical imaging device development and optimization, system inter-comparison, clinical trial standardization, constancy testing, recalibration, manufacturing quality assurance, and regulatory evaluation. While there has been significant work on developing phantoms for biophotonic imaging systems, there are no solid, stable, phantom materials containing hemoglobin in its native conformation.

In order to account for the impact of Hb absorption, many prior phantom designs have either incorporated Hb or a combination of dyes that simulate the optical absorption of Hb. These phantoms can be divided into three categories: liquid solutions, gels, and solid polymers. The first two categories enable the incorporation of Hb, thus providing biologically realistic spectral variations in absorption over large ranges. Liquid phantoms, often involving the fat emulsion infusion Intralipid or polymer microspheres as scatterers, have been broadly used because of their convenience in fabrication (including the addition of a range of dyes and biological absorbers including Hb) as well as their flexibility in performing measurements. However, liquid phantoms suffer from several key drawbacks. First, it is difficult to fabricate liquid phantoms that mimic inhomogeneous structures incorporating multiple layers or vascular structures. Second, liquid phantoms lack stability because their optical properties change over time through evaporation, settling, or biological changes.

Phantoms using gelatinous substances can overcome some disadvantages of liquid phantoms, such as construction of basic geometric shapes. However, gelatinous phantoms are fragile and crumble under applied stress. They contain a solvent, which evaporates and induce alteration in dimensions and optical properties of the phantoms. While hydrogel-based phantoms can have realistic oxyhemoglobin absorption in the UV and visible region, the stability of hydrogel phantoms tends to be a few days or weeks and they typically have low mechanical strength. Furthermore, hydrogels often require high heating to induce setting, which may affect biological components such as Hb.

In contrast, the solid Hb-silicone (e.g., PDMS) material disclosed herein is easy to mold, stable for months (such as about two months, about 6 months or up to one year), and non-toxic during preparation and application. The ability to fabricate holes or channels makes it possible to generate phantoms with heterogeneous optical properties. This feature enables evaluation of detectability of target objects having different tissue-like contrast so that contrast-detail analysis and similar evaluations can be performed with the disclosed phantoms. Further, the capability of manufacturing layered phantoms though sequential casting with different oxygenation levels of Hb makes it feasible to create anatomically realistic phantoms for clinical uses.

The solid Hb-silicone (e.g., PDMS) material disclosed herein can be incorporated into a wide range of phantoms for in vivo biophotonic diagnostic devices in which blood-based biomarkers are used or in which Hb represents a potential confounding factor. Devices that use Hb for oximetry measurements include HRI, and NIRS systems. Several commercially-available systems based on these approaches are in common clinical use for evaluation of Hb saturation levels in cerebral and general tissue (e.g., muscle) oximetry. In some embodiments, the solid Hb-silicone (e.g., PDMS) material can be incorporated into phantoms that have been designed to represent cerebral morphology including vascular structures that have Hb absorption characteristics, in order to evaluate characteristics such as penetration depth, repeatability, tissue oxygenation measurement accuracy, etc. In some embodiments, the solid Hb-silicone (e.g., PDMS) material can also be incorporated into phantoms designed to represent vascular tissue during intraoperative HRI, for evaluation of resolution and the effect of vessel size on detectability. The solid Hb-silicone (e.g., PDMS) material can also be used as a confounding absorber in phantoms designed to test the performance of devices like endoscopic fluorescence imaging systems for cancer detection.

In some embodiments, the matrix material of the disclosed Hb-silicone phantoms is liquid-form silicone, PDMS (Sylgard® 184 Silicone Elastomer DOW/Corning). One advantages of solid phantoms involving polymers such as PDMS is that they can include nonorganic scatters and absorbers to mimic the optical properties of tissues. The performance of optical medical devices can be sensitive to the optical interface, which depends on the mechanical properties of phantoms and the index refraction. The disclosed Hb-PDMS phantoms have a soft, rubber-like texture after curing, are robust relative to gelatinous phantoms, and have more appropriate mechanical properties close to that of tissue than harder materials such as polyester plastics. Furthermore, PDMS has a refractive index of about 1.4 in the near infrared spectrum, which is in the range of the refractive index of tissues. In contrast, the commonly used bulk matrix phantoms have a corresponding refractive index of 1.35 in aqueous suspension, gelatin/agar matrix, Polyvinyl alcohol gel, and Polyacrylamide gel, or 1.5 in epoxy resin.

In manufacturing solid tissue-simulating phantoms, approaches employing silicone polymers such as PDMS with water based dyes, Hb, or blood are unexpected because PDMS is hydrophobic and difficult to mix evenly (e.g, homogeneously) with an aqueous solution. For example, in a prior attempt to mix blood with silicone to simulate optical properties of human skin in a solid phantom, the end product was "not stable over time" (Lualdi et al., Lasers in Surgery and Medicine, 28:237-243, 2001).

To overcome the difficulty of mixing Hb with a hydrophobic silicone material such as PDMS, a novel fabrication process was developed that involves sonication and low temperature curing to generate a solid phantom containing human Hb in its native conformation (not denatured). The resulting solid phantoms exhibit realistic spectral properties of Hb and little variation in optical properties over months.

I. Summary of Terms

As used in this application and in the claims, the singular forms "a," "an," and "the" include the plural forms unless the context clearly dictates otherwise. Additionally, the term "includes" means "comprises." The disclosed systems, methods, and apparatus are not limited to any specific aspect or feature or combinations thereof, nor do the disclosed systems, methods, and apparatus require that any one or more specific advantages be present or problems be solved. Any theories of operation are to facilitate explanation, but the disclosed systems, methods, and apparatus are not limited to such theories of operation.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

Unless context indicates otherwise, all technical and scientific terms used herein have the same meaning as commonly understood to one of ordinary skill in the art to which this disclosure pertains. Although methods and materials similar or equivalent to those described herein can be used in the practice or testing of the present disclosure, suitable methods and materials are described below. The materials, methods, and examples are illustrative only and not intended to be limiting. In case of conflict, the present specification, including explanations of terms, will control.

About: With reference to a numerical parameter, the term "about" refers to a plus or minus 5% range around the numerical parameter. For example, "about 5%" refers to "4.75% to 5.25%."

Desaturation agent: A substance or combination of substances that desaturates oxygenated Hb to yield deoxygenated Hb. Non-limiting examples of desaturation agents include yeast powder and sodium dithionite. See, e.g., Yang et al., "Low-cost frequency-domain photon migration instrument for tissue spectroscopy, oximetry, and imaging", Opt. Eng., 36, 1562, 1997 (use of yeast); Vandegriff and Olson, "The kinetics of 02 release by human red blood cells in the presence of external sodium dithionite", J. Biol. Chem., 259, 12609, 1984 (use of sodium dithionite). Desaturation of Hb can also be achieved using nitrogen gas (e.g., as described in Hyttel-Sorensen et al., "Calibration of a prototype NIRS oximeter against two commercial devices on a blood-lipid phantom", Biomed. Opt. Exp., 4, 1662, 2013).

Hemoglobin (Hb): An iron-containing metalloprotein located in the red blood cells of vertebrates and other animals which functions to transport oxygen and carbon dioxide in the blood. Vertebrate Hb consists of four polypeptide chains, each containing an iron-containing heme group. Deoxygenated hemoglobin is hemoglobin that is not bound to oxygen.

Oxygenated hemoglobin refers to hemoglobin that is saturated with oxygen, for example, having an oxygen saturation level of more than 90%. Deoxygenated hemoglobin refers to hemoglobin that is desaturated with oxygen, for example, having an oxygen saturation level of less than 10%. Partially oxygenated hemoglobin is hemoglobin comprising an oxygen saturation level of from 10% to 90%. Hemoglobin for use in manufacturing the disclosed biophotonic phantoms can be obtained commercially (for example, purified Hb solution, Level 2, Multi-4 Co-Oximetry controls, Instrumentation Laboratory Co., Bedford, Ma).

Hemoglobin in a native conformation: Hemoglobin that is not denatured and can bind to oxygen.

Hemoglobin distributed in a solid polymer matrix: A hardened (cured) polymer resin containing Hb, for example, that is dispersed throughout the cured polymer, and in some embodiments is evenly dispersed. Several embodiments provide a solid matrix of cured PDMS comprising Hb that is homogeneously distributed throughout the cured PDMS polymer. As used herein, "homogeneous" distribution means that the fraction of Hb that is present in relatively pure amorphous domains within the solid polymer matrix is relatively small, on the order of less than 5%, and preferably less than 1% of the total amount of Hb in the relevant polymer matrix. In other embodiments, a solid matrix of cured PDMS comprising Hb distributed in a spatial gradient is provided.

Image: A set of data points representative of a spatially resolved parameter, such as a set of spatially resolved values, where each data point corresponds to a value of a parameter (such as ultrasonic signal intensity) in a position. The positions may be comprised within a plane, corresponding to a one-dimensional or two-dimensional image, or they may be distributed across more dimensions, for example three dimensions. Further, each data-point may correspond to a finite area or volume, such as having a finite area or finite volume being assigned to each data point, although the position is described as a mathematically ideal point in space. In several embodiments, an image can be displayed on a screen, for example, for view by a user.

Biophotonic Phantom: A synthetic object that can be scanned (for example, three-dimensionally scanned) or imaged using an optical detection system (such as a NIRS detection system) or device to evaluate, analyze, and/or calibrate the performance characteristics of the detection system or device. Biophotonic phantoms are preferred to living or dead tissue for testing and calibrating detection systems and devices as they are more convenient, more temporally and mechanically stable, and can be standardized to provide more consistent results than the living or dead tissue, and can be designed to have inclusions (such as an array of microwires), for determining image quality characteristics, such as the spatial resolution of a NIRS imaging system. Phantom-based test and calibration methods are commonly used in medical imaging device development and optimization, system inter-comparison, benchmarking, clinical trial standardization, constancy testing, recalibration, quality assurance, training, education, and regulatory evaluation.

Biophotonic phantoms are an effective tool for evaluating imaging system performance and assessing image quality. The biophotonic phantoms of the present disclosure can be used in several applications for optical detection systems (such as NIRS and HRI systems), including but not limited to: 1) to ensure imaging system quality in the manufacturing process and provide end users with qualification of a delivered system; 2) to ensure consistent nominal image system performance over time; 3) to validate re-calibration during servicing, maintenance, and repair of imaging systems with degraded performance; 4) to compare the performance of different imaging systems, 5) as marketing tools to enable companies to gather objective, quantitative evidence of imaging system efficacy, and 6) as education tools to train users how to operate an optical detection system of interest.

Optical beams, optical radiation, and light: Propagating electromagnetic radiation at wavelengths between about 200 nm and 3000 nm. The term "optical beam" is used for convenient description and does not imply any particular beam collimation, and as used herein, optical beams can be associated with numerical apertures as large as 1. Visible wavelengths of light are generally from 400-700 nm. Near infrared wavelengths of light are generally from 700 to about 1000 nm. In several embodiments, the disclosed phantoms can simulate the optical response of tissue to light in visible and near infrared wavelengths such as from 400-1000 nm.

Polydimethylsiloxane (PDMS): A type of liquid-form silicone that is optically clear and that can be cured (hardened) into a solid matrix by addition of an appropriate curing agent (cross-linker). As disclosed herein, PDMS can be cured using a curing process that be performed at room temperature. PDMS and relevant curing agents for use in manufacturing the disclosed phantoms can be obtained commercially (for example as Sylgard® 184 Silicone Elastomer, Dow Corning, Midland, Mich.).

PDMS is cured by an organometallic crosslinking reaction. The curing agent induces the crosslinking reaction. The siloxane base oligomers in PDMS contain vinyl groups. The cross-linking oligomers contain at least 3 silicon hydride bonds each. In several embodiments (such as those using Sylgard® 184 Silicone Elastomer), the curing agent contains a platinum-based catalyst that catalyzes the addition of the SiH bond across the vinyl groups, forming Si—$CH_2$—$CH_2$—Si linkages. The multiple reaction sites on both the base and crosslinking oligomers allow for three-dimensional crosslinking (see, e.g., Campbell et al., "Replication and Compression of Bulk Surface Structures with Polydimethylsiloxane Elastomer." J. Chem. Educ., 76, 537, 1999).

Silicone: As used herein, "silicone" refers to siloxane polymers in liquid form that can be hardened into a solid matrix by addition of a curing agent and using a curing process that can be performed at room temperature.

II. Phantoms

Novel phantoms for assaying, calibrating, and/or testing the performance of an optical detection system (such as a NIRS imaging system) are provided. The disclosed phantoms comprise Hb in a native conformation that is distributed (such as homogenously distributed) in a solid matrix of cured silicone, such as PDMS.

By altering the constituents of the phantom, the optical properties of the phantom may be tuned to simulate the corresponding optical properties of many different tissues of interest. Thus, the phantom enables accurate simulation of many distinct tissue types and compositions that cannot be achieved with prior phantom materials. In several embodiments, the phantom can be molded to represent an anatomical body region, part, or organ containing multiple tissue types.

The solid matrix of cured PDMS comprising Hb in its native conformation included in the biophotonic phantom maintains an attenuation coefficient and an absorption coefficient that remain stable (for example, that change no more than 10%) across visible and/or near infrared wavelengths (for example, 400-1000 nm light) over time, such as at least two months (for example, about two months, about 6 months, or up to one year) following curing of the PDMS in the matrix. In some embodiments, the In some embodiments, the solid matrix of cured PDMS in the biophotonic phantom can comprise from 0.0001 to 5% Hb by weight. For example the solid matrix of cured PDMS in the biophotonic phantom can comprise from 0.001% to 5%, from 0.01% to 5%, from 0.1% to 5%, from 0.5% to 5%, from 1.0% to 5%, from 1.5% to 5%, from 2.5% to 5%, from 0.001% to 2.5%, from 0.01% to 2.5%, from 0.1% to 2.5%, from 0.5% to 2.5%, from 1.0% to 2.5%, from 1.5% to 2.5%, from 0.01% to 2%, from 0.1% to 2%, from 0.5% to 2%, from 1.0% to 2%, from 1.5% to 2%, from 0.01% to 1%, or from 0.1% to 1% Hb by weight. In additional embodiments, the solid matrix of cured PDMS in the biophotonic phantom can comprise about 0.0001%, about 0.001%, about 0.01%, about 0.1%, about 0.5%, about 0.8%, about 1.0%, about 1.2%, about 1.5%, about 1.8%, about 2.0%, about 2.2%, about 2.5%, about 3%, about 4%, or about or about 5% Hb by weight. In a preferred embodiment, the solid matrix of cured PDMS in the biophotonic phantom can comprise from about 1.0% to about 2.5% Hb by weight. In another preferred embodiment, the solid matrix of cured PDMS in the biophotonic phantom can comprise about 1.8% (such as 1.8%) Hb by weight.

In some embodiments, the solid matrix of cured PDMS in the biophotonic phantom can comprise from 0.5 to 25% Hb by weight. For example the phantom can comprise from 1% to about 10%, from about 5% to about 10%, from about 5% to about 15%, from about 5% to about 20%, from about 7% to about 10%, from about 7% to about 11%, from about 7% to about 12%, from about 8% to about 10%, from about 8% to about 11%, from about 8% to about 12%, from about 9% to about 10%, from about 9% to about 11%, from about 9% to about 12%, from about 10% to about 12%, from about 10% to about 15%, from about 10% to 20%, or from about 15% to about 20% Hb by weight. In additional embodiments, the Hb-silicone (e.g., Hb-PDMS) phantom comprises from 1% to 10%, from 5% to 10%, from 5% to 15%, from 5% to 20%, from 7% to 10%, from 7% to 11%, from 7% to 12%, from 8% to 10%, from 8% to 11%, from 8% to 12%, from 9% to 10%, from 9% to 11%, from 9% to 12%, from 10% to 12%, from 10% to 15%, from 10% to 20%, or from 15% to 20% m/m PVC/binary plasticizer. In additional embodiments, the Hb-silicone (e.g., Hb-PDMS) phantom can comprise about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% Hb by weight. In additional embodiments, the Hb-silicone (e.g., Hb-PDMS) phantom can comprise 2%, 3%, 4%, 5%, 6%, 7%, 8%, 9%, 10%, 11%, 12%, 13%, 14%, 15%, 16%, 17%, 18%, 19%, or 20% Hb by weight. In a preferred embodiment, the Hb-silicone (e.g., Hb-PDMS) phantom can comprise from about 8% to about 14% Hb by weight. In another preferred embodiment, the Hb-silicone (e.g., Hb-PDMS) phantom can comprise about 12% (such as 12%) Hb by weight.

In some embodiments, an amount of Hb in the solid matrix of cured PDMS in the biophotonic phantom can be selected that mimics bruised or normal (not-bruised) tissue.

The Hb included in the disclosed phantoms can be purified from blood isolated from a subject (for example a human subject). In some embodiments, the Hb can be obtained commercially (for example, purified Hb solution, Level 2, Multi-4 Co-Oximetry controls, Instrumentation Laboratory Co., Bedford, Ma).

A pre-selected amount of curing agent is used to cross link the liquid form silicone (such as PDMS) in the disclosed phantoms. In some embodiments, the phantom comprises a ratio of curing agent to silicone (such as PDMS) of from 1:5 to 1:15, such as 1:8 to 1:15, 1:9 to 1:11, or about 1:10, or 1:10. The ratio of curing agent to silicone in the Hb-silicone phantom can be altered as needed to increase or decrease phantom mechanical stiffness, or to control other characteristic of the phantom, such as optical or acoustic properties.

In some embodiments, the phantom material can be encased in a low gas permeability polymer shell to reduce the rate of Hb re-oxygenation over time. In some embodiments, the shell can be a thin sheet of low gas permeability polymer (<1 mm) with high optical transmittance (>90%, such as at least 95% or at least 99%) over visible and near-infrared wavelengths (e.g., 400-1000 nm). In some embodiments, the disclosed biophotonic phantom material can be cured and encased in a thin shell of poly(vinyl alcohol) (PVA) film which has low oxygen permeability. PVA films can be prepared, for example, by drying a 3 mm thick, water solution of 1% PVA (Cat#341584, Sigma-Aldrich) at room temperature in a petri dish (the dried film is <0.3 mm thick). In some embodiments, the phantom material can be encased in optical cuvettes made of polymethacrylate (Cat#C0793, Sigma-Aldrich), capped with cuvette stoppers made of polyethylene (Fisherbrand™). In some embodiments, the phantom material in the cuvettes can be placed within a polyethylene/nylon material, and thermally sealed with a vacuum sealer.

Additives

The biophotonic phantom can further comprise additives with optical absorbing, optical scattering, acoustic absorbing, and/or acoustic scattering properties to modify the acoustic and/or optical properties of the phantom to mimic a selected tissue. The additives are typically added to the Hb-silicone mixture prior to or during the curing process.

In some embodiments, the phantom can include one or more optical absorbing additives. Exemplary optical absorbing additives include dyed polymer microparticles, dyed glass microparticles, metal particles, metal microparticles, carbon black, India ink, nigrosin, and black plastic colorant (BPC). The Hb-silicone phantom can include the optical absorbers at an appropriate concentration for the Hb-silicone phantom to mimic the optical properties of a selected tissue.

In some embodiments, the phantom can include one or more optical scattering additives. Exemplary optical scattering additives include barium sulfate, polystyrene or silica microparticles having a diameter of from 0.5-10 μm, and titanium dioxide ($TiO_2$, such as anatase, such as anatase $TiO_2$ with mean particle/agglomerate diameter of 25-1000 nm, such as 500 to 600 nm). The phantom can include the one or more optical scattering additives at an appropriate concentration for the Hb-silicone phantom to mimic the optical properties of a selected tissue.

In several embodiments, the phantom can be formulated to mimic the optical properties of a particular tissue type, such as fatty breast tissue, breast tissue with moderate relative fat/parenchyma content, parenchymal breast tissue, skin, adipose, brain, liver, esophagus, cervix or skeletal muscle. The optical properties of such phantoms are of superior biological relevance compared to prior phantoms due to the presence of actual hemoglobin (as opposed to additives that mimic hemoglobin).

To mimic particular tissue of interest the phantom is constructed with appropriate additives to simulate the optical properties (absorption coefficients and scattering coefficients) of the tissue of by adding scattering materials and absorption materials to the Hb-silicone phantom interest (see, e.g., Steven L Jacques, "Optical properties of biological tissues: a review", Phys. Med. Biol. 58, R37-R61, 2013, Utzinger et al., Lasers Surg. Med. 28(1), 56-66, 2001; Drezel et al., Cancer 98, 2015-2027, 2003. Each of which is incorporated by reference herein in its entirety). In some embodiments, the phantom can include an appropriate amount of hemoglobin to represent normal skin (0.3 mg/g Hb conc., 0.29 g/L) or freshly bruised skin (4.5 mg/g Hb con., 4.34 mg/L), with 1.72% (wt/wt) $BaSO_4$ to produce $\mu_s'$=13/cm at 800 nm and 0.0055% (wt/wt) India Ink (and optionally an appropriate amount of nigrosine) to match the base absorption of skin without blood in the NIR range.

Inclusions/Targets

One or more heterogeneous inclusions or targets can be included in the disclosed phantom to be used in calibrating or testing the performance of an optical or acoustic detection system, such as a NIRS system and a HRI system. For example, phantoms incorporating targets/inclusions may be used to evaluate the image quality of a NIRS system. Non-limiting examples of suitable materials include thin filaments such as metal wires and nylon suture wires for sub-resolution targets, solid inclusions of PDMS material with differing properties from the surrounding PDMS phantom (such as a greater or reduced concentration of Hb), and fluid channels or embedded tubing injected with absorptive dye solutions.

In some embodiments, the Hb-silicone (e.g., PDMS) material can be shaped into an inclusion that is embedded in a turbid matrix to serve as a target for testing and/or calibrating the performance of an optical detection device (e.g., penetration depth, sensitivity, spectral measurement accuracy, etc.).

In some embodiments, the Hb-silicone (e.g., PDMS) material can be used as an inclusion in a biophotonic phantom for evaluating oxygen saturation measurement accuracy of a detection device. For example, a disclosed phantom can be constructed to include one or more segments (e.g., inclusions) made of the disclosed Hb-PDMS polymer that has a known level of Hb saturation. The segments (e.g., inclusions) can have an Hb-saturation level that is different from the material adjacent to the segment in the phantom. In some embodiments, a set of Hb-PDMS phantoms can be provided, with each phantom in the set having a different Hb-saturation level. The set of Hb-PDMS phantoms can be used to calibrate devices used to detect Hb-saturation levels in a tissue or subject.

In some embodiments, the inclusion can be a hollow inclusion that is filled with a liquid solution (e.g., Hb/scatterer/fluorophore solutions).

Arrays of heterogeneous inclusions or targets can be used to quantitatively and objectively assess image quality of an optical detection system, such as a NIRS imaging system and a HRI system. There are multiple uses for such an array, including measurement of axial resolution, lateral resolution, elevational resolution, spatial measurement accuracy, sensitivity, signal-to-noise ratio, dynamic range, image uniformity, distortion, and image artifacts.

In some embodiments, one or more filaments (such as an array of regularly spaced filaments) may be embedded in the Hb-silicone phantom to provide a series of targets for the purpose of measuring spatial resolution (in the axial, lateral, and elevational directions), spatial distance measurement accuracy, image uniformity, and geometric distortion, of a detection system, such as a NIRS system and a HRI system. Array targets are desired which produce high optical signal, but can withstand the manufacturing process for the Hb-silicone phantom. These filaments may be metal wires, such as aluminum, nickel, steel, or tungsten, or polymeric materials, including dyed (e.g. blue, black) nylon suture wire. Monofilament sutures can be used as point targets for imaging applications.

In some embodiments, one or more solid inclusions (such as an array of regularly spaced solid inclusions) may be embedded within the Hb-silicone phantom. By varying inclusion size, depth, and absorption strength, quantitative analysis can provide performance metrics such as image penetration depth, contrast-to-noise ratio, signal-to-noise ratio, uniformity within the image plane, low-contrast detectability, image artifacts, and sensitivity, of a detection system, such as a NIRS system. Non-limiting examples of materials that can be used for the solid inclusion include Hb-silicone materials having different optical and/or acoustic properties compared to surrounding Hb-silicone phantom, other gels such as other plastisols, hydrogels, or polymer gels. The solid inclusions can have higher, lower, or equal optical properties relative to a surrounding phantom medium.

In some embodiments, one or more fluid channels (such as an array of regularly spaced fluid channels) may be used to enable contrast-detail analysis with liquid solutions containing light-absorbing molecules. Non-limiting examples of methods of forming fluid channels include 1) suspending metal wires/rods and cast-molding the Hb-silicone material around them, then withdrawing the wires from the cured Hb-silicone, or 2) embedding transparent lengths of tubing in Hb-silicone phantom. After the fluid channels are formed in the Hb-silicone phantom, they can be filled with the liquid solutions containing optical or acoustic absorbing and/or scattering molecules. By varying fluid channel size and depth, and the absorption/scattering strength of any injected fluid, quantitative analysis can provide performance metrics such as image penetration depth, contrast-to-noise ratio, signal-to-noise ratio, uniformity within the image plane, low-contrast detectability, image artifacts, and sensitivity, of a detection system, such as a NIRS system.

Non-limiting examples of absorbing molecules that can be included in a liquid solution injected into a fluid channel include biological molecules such as oxyhemoglobin, deoxyhemoglobin, methemoglobin, and carboxyhemoglobin, as well as exogenous molecules such as nanoparticles, cyanine dyes, and methylene blue. Additional examples of absorbing molecules that can be included in the liquid injected into the fluid channel include chromophores, fluorophores, and/or photosensitizers, including but not limited to gold nanoparticles (nanoshells, nanorods), indocyanine green, other cyanine dyes, fluorescein, Cy5, Cy7, protoporphyrin IX, and bioconjugated fluorescent tags and biomarkers. After injection of the liquid solution, the fluid channels can be sealed shut to prevent changes in liquid solutions due to environmental effects.

The phantom can also include one or more complex inclusions embedded within the Hb-silicone material, such as a tumor simulator (e.g., a solid inclusion simulating tumor tissue surrounded by liquid and/or differing solid inclusions that simulate the tumor microenvironment and vasculature), or one or more channels simulating complex vasculature.

Phantom Shape

Figure 1B:
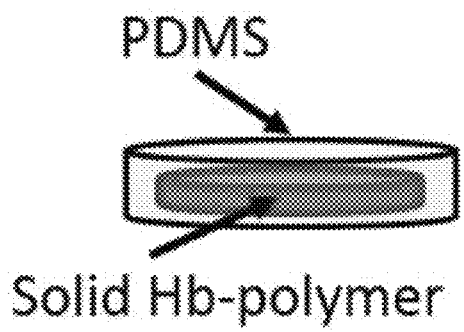
Figure 1C:
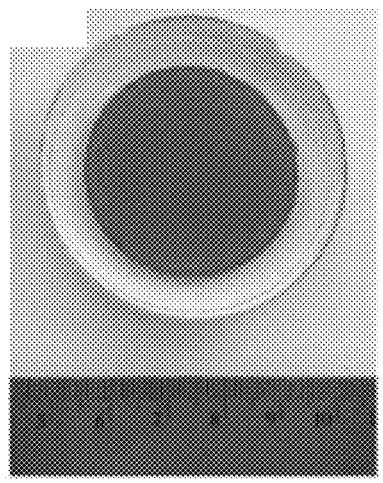
Figure 2A:
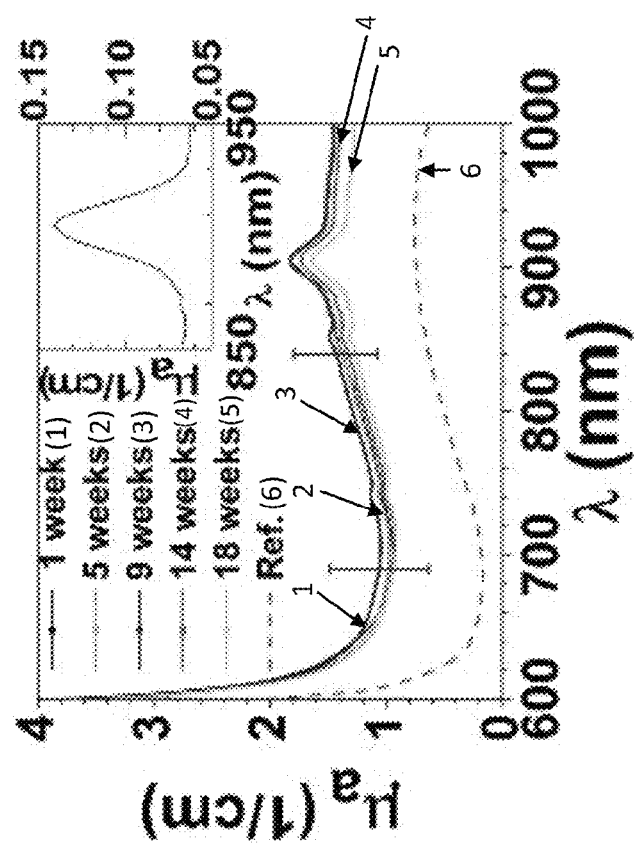
FIGS. 2A-2D are a set of graphs showing the total attenuation coefficient ($\mu_t$) and absorption coefficient ($\mu_a$) of oxygenated Hb-PDMS phantoms encased in a 4 mm shell of Hb-free PDMS at selected time intervals across the (FIG. 2A) visible and (FIG. 2B) near infrared spectra. $\mu_a$ measurements at visible (FIG. 2C) and near infrared (FIG. 2D) spectra were also obtained one year following phantom construction. The dashed line shows the rescaled absorption spectra of diluted human blood (from Prahl et al., Appl. Opt., 32, 559 (1993)). The absorption of PDMS is shown in the inserted graph in (FIG. 2B). In between use, the phantoms were kept in sealed nitrogen-filled containers at 4° C.
Figure 2B:
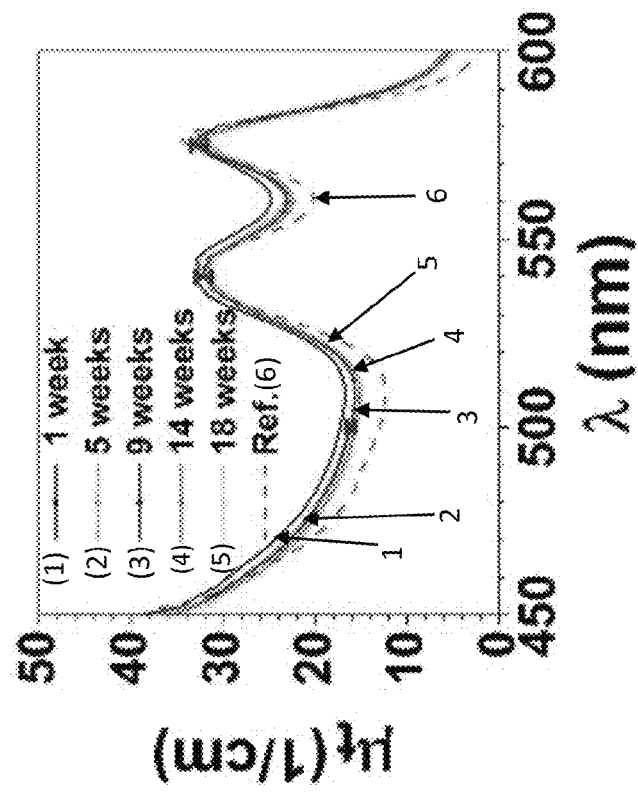
Figure 2C:
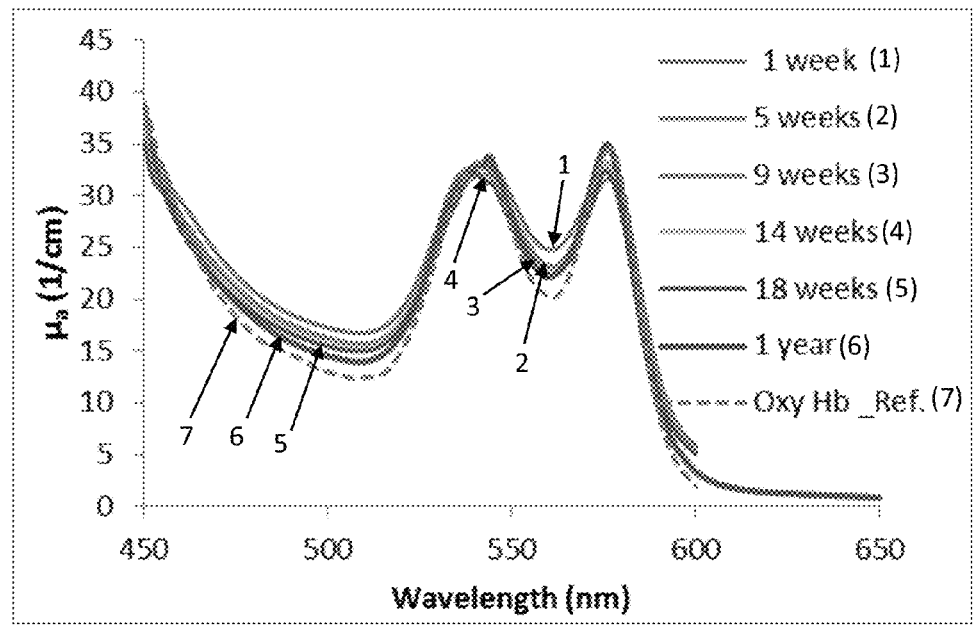
Figure 2D:
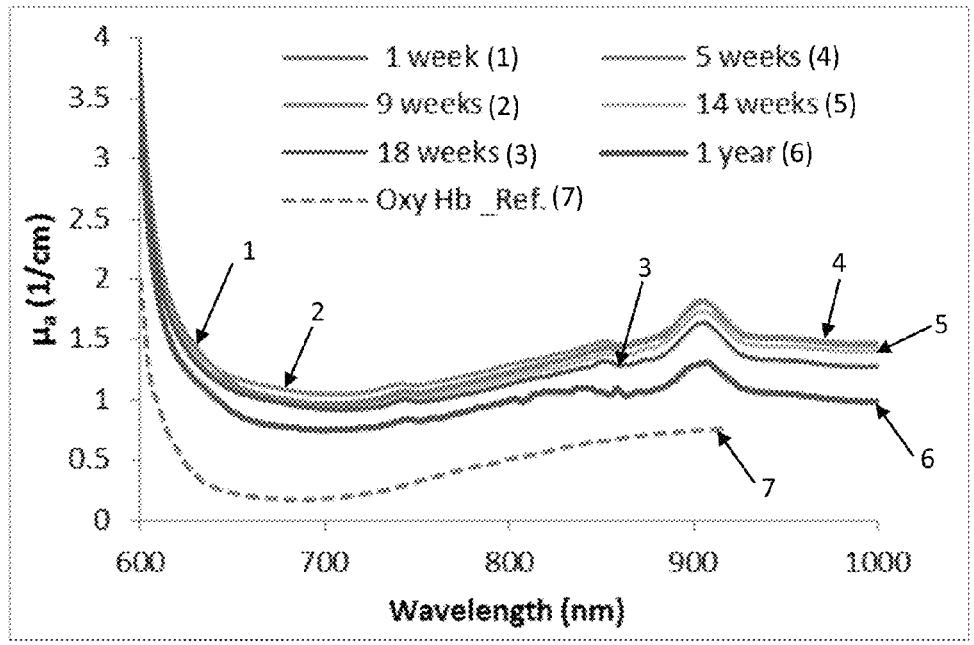

The disclosed phantoms can have any shape or size appropriate for the intended use. Typically the phantom is cast-molded into a particular pre-selected shape and size of interest. For example, the phantom can be molded into a cube, cuboid, sphere, ellipsoid, or cylinder shape. FIGS. 1, 9, and 10 show illustrative embodiments of the disclosed phantoms having a cubical or cylindrical shape. FIGS. 1B and 1C illustrate a Hb-PDMS phantom having a cylindrical shape that is approximately 4 cm in diameter. FIG. 10A illustrates exemplary biophotonic phantom 202 having a cylindrical shape with a diameter that is longer than its height. In another embodiment, biophotonic phantom 206 shown in FIG. 10C has a cubical shape.

In some embodiments, the phantom can be molded into the shape of a body part or tissue of interest. In some embodiments, multiple Hb-silicone (e.g., Hb-PDMS) phantoms with tissue-specific properties can be molded into shapes representing different parts or tissues of a body region of interest containing multiple organs and/or tissue types (such as a brain) and then incorporated into a single multimeric phantom. For example, multimeric phantoms representing complex biological organs, body parts, systems, and even small organisms (such as a mouse) can be generated by constructing the phantom using a plurality of Hb-silicone phantoms, with each phantom in the plurality modified as needed with additives and/or inclusions to simulate a particular tissue or component of the organ, body part, system, or small organism.

In some embodiments, the disclosed biophotonic phantoms can be encased in a shell of material that does not contain Hb. In several embodiments, the shell can be made of the same polymer material (such as PDMS) from which the phantom is constructed. The shell provides a layer that inhibits exposure of the Hb-PDMS phantom material to air, thereby inhibiting changes in the oxygenation level of the Hb in the phantom. The thickness of the shell encasing the Hb-PDMS material can vary as needed. In several embodiments, the shell can be from 3-5 mm thick, such as about 4 mm thick. FIGS. 10B and 10D show illustrative embodiments of the disclosed phantoms having a cubical or cylindrical shape that are encased in a shell of material that does not contain Hb. FIG. 10B illustrates exemplary biophotonic phantom 202 having a cylindrical shape with a diameter that is longer than its height, and that is encased in Hb-free shell 204, which also has a cylindrical shape. In another embodiment, biophotonic phantom 206 shown in FIG. 10C has a cubical shape and is encased in Hb-free shell 208, which also has a cylindrical shape.

Phantom Manufacture

Figure 8:
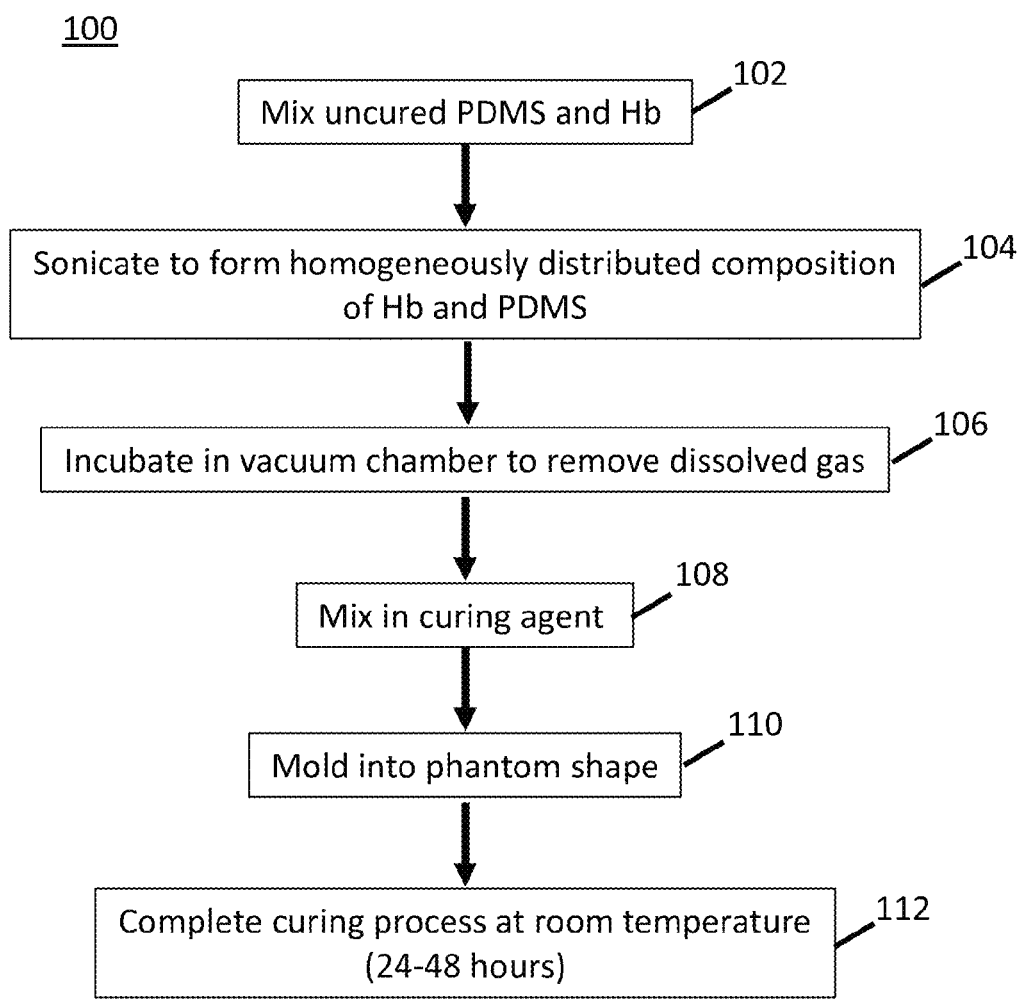
FIG. 8 is a flow chart illustrating an exemplary embodiment of a process for producing a disclosed solid Hb-PDMS phantom.

Methods of producing the disclosed phantoms are also provided. FIG. 8 illustrates an exemplary multi-step process 100 for manufacturing a Hb-PDMS phantom as disclosed herein. Using the disclosed process, it is possible for the first time to manufacture a solid matrix biophotonic phantom containing hemoglobin in its native conformation.

As shown in FIG. 8 at process block 102, the process 100 begins by mixing uncured PDMS and Hb together at a pre-selected ratio. The uncured PDMS is liquid form PDMS, for example PDMS included with Sylgard® 184 Silicone Elastomer (Dow Corning, Midland, Mich.). The Hb can be a Hb solution (for example, purified Hb solution, Level 2, Multi-4 Co-Oximetry controls, Instrumentation Laboratory Co., Bedford, Ma).

At process block 104, the mixture of Hb and PDMS is sonicated to form a homogeneously distributed composition of Hb and PDMS. To inhibit Hb denaturation, and/or oxidation to methemoglobin, the sonication is performed without overly heating the Hb-PDMS mixture. For example, the sonication comprises episodes of sonication separated by intervals that permit sufficient heat dissipation to inhibit thermal denaturation of the Hb and/or its oxidation to methemoglobin. In some embodiments, the uncured PDMS and Hb can be incubated at a cool temperature (such as 0-10° C.) during the sonication step (for example by using an ice-water bath) to further inhibit heating of the uncured PDMS and Hb mixture and any corresponding Hb denaturation and/or oxidation. The sonication can be performed for a duration of from 8-12 hours (such as about 10 hours). In some embodiments, the sonication can be performed using a Qsonica Sonicator (Newton, Conn.) with a pulsed on-off setting of 3-5 seconds and 30-50 seconds (such as 37 seconds), respectively, at an amplitude of 20% for 8-12 hours (such as about 10 hours).

At process block 106, the homogeneously distributed composition of Hb and PDMS is placed into a vacuum chamber to remove dissolved gas that could have been introduced by the preceding process steps. For example, the vacuum can be applied for a duration of from 5 to 10 hours (such as about 6 hours).

At process block 108, the curing agent is mixed into the homogeneously distributed composition of Hb and PDMS. An amount of curing agent can be used that results in an appropriate level of PDMS cross-linking and resulting phantom mechanical stiffness. In some embodiments, the curing agent is added at a ratio of from 1:5 to 1:15 (such as about 1:10) by weight curing agent to PDMS. The curing agent is mixed into the homogeneously distributed composition of Hb and PDMS an appropriate amount of time, such as from 3-7 minutes, for example about 5 minutes.

Following addition of curing agent, the homogeneously distributed composition of Hb and PDMS is molded into an appropriate size and shape for the desired biophotonic phantom (process block 110).

At process block 112, the curing process is completed by incubating the homogeneously distributed composition of Hb and PDMS at room temperature. After 24-48 hours, the curing process is typically complete.

As illustrated in FIG. 1B, the Hb-PDMS phantom can optionally be encased in a shell of PDMS material that does not contain Hb. In some embodiments, the phantom material can be encased in a low gas permeability polymer shell to reduce the rate of Hb re-oxygenation over time. The presence of the PDMS shell inhibits exposure of the Hb in the Hb-PDMS phantom to air, thereby inhibiting changes in the oxygenation level of the Hb in the phantom. The thickness of the shell encasing the Hb-PDMS material can vary as needed. In several embodiments, the shell can be from 3-5 mm thick, such as about 4 mm thick. In some embodiments, the shell can be a thin layer of PVA material that has low or no gas permeability.

After construction, the Hb-PDMS phantom can be stored under appropriate conditions. For example, the phantom can be stored at 4° C. under nitrogen gas to maintain stability and inhibit changes in the oxygenation level of the Hb in the phantom.

In several embodiments, the Hb in the phantom can be deoxygenated. In such embodiments, an effective amount of a desaturation agent is added to the phantom during the manufacturing process to deoxygenate the Hb. The desaturation agent can be, for example, yeast powder or sodium dithionite. The desaturation agent can be added to the Hb-PDMS composition at any appropriate time during the manufacturing process of the phantom. In some embodiments, the desaturation agent can be added to homogeneously distributed composition of Hb and PDMS following process step 104 in the method described above. In some embodiments, the desaturation agent can be added to homogeneously distributed composition of Hb and PDMS along with (or shortly thereafter) addition of the curing agent during process step 108 in the method described above.

In embodiments wherein the phantom has one or more embedded inclusions or targets, the inclusion or target can, for example, be included in the mold into the Hb-PDMS composition is poured. In embodiments wherein the phantom has one or more fluid channels, the fluid channels can, for example, be formed by including one or more retractable wires in the mold, and then retracting the wires from the mold after the Hb-PDMS composition has cured to a solid matrix to form the fluid channels. Additives can be mixed with the Hb-PDMS at any point before or during addition of the curing agent.

III. Detection Systems

The disclosed phantoms provide realistic simulations of the optical and/or acoustic properties of tissue. Accordingly, the phantoms can be used with a wide range of optical or multi-modal imaging/diagnostic systems involving optical radiation delivery or detection where it is desirable to use a phantom that simulates the optical properties of a tissue or organ, for example, to calibrate or test the performance of the detection system (Pogue, et al. J. Biomed. Opt. 11, 041102, 2006). Non-limiting examples of optical and multi-modal detection systems for use with the disclosed phantoms are discussed below.

Optical Detection Systems

Because the disclosed phantoms have realistic tunable optical properties, they are suitable for evaluating performance of medical optical imaging/diagnostic systems. While imaging systems inherently provide information on the spatial distribution of features and signals in tissue, optical spectroscopy systems provide information on the wavelength-dependence of optical signals using non-imaging probes/detectors (see, e.g., Biomedical optics: principles and imaging; L V Wang, H Wu, John Wiley & Sons, 2012). Spectral/hyperspectral imaging approaches provide information on both spatial and wavelength-dependent variations. The disclosed Hb-silicone (e.g., Hb-PDMS) phantoms can be used to assess imaging and spectroscopy modalities wherein Hb is a biomarker and/or a confounder, such as the following:

Near-Infrared Spectroscopy (NIRS).

NIRS is a quantitative (non-imaging) approach involving measurement of near-infrared radiation at one or more wavelengths which is delivered to and reflected from tissue (see, e.g., Near-infrared spectroscopy: principles, instruments, applications, H W Siesler, Y Ozaki, S Kawata, H M Heise, Wiley-VCH, 2008; Progress of near-infrared spectroscopy and topography for brain and muscle clinical applications, M Wolf, M Ferrari, V Quaresima—J Biomed Opt, 12(6), 062104, 2007). NIRS is typically used to measure Hb concentration and/or oxygenation, or the presence/concentration of other endogenous or exogenous chromophores. Commercially available clinical NIRS systems are often oximeters that perform skin contact probe measurements with fixed illumination-collection separation at two or more wavelengths based on the spectral absorption characteristics of oxy- and deoxy-Hb. The applications of these devices include evaluation of skin tissue viability and cerebral tissue health status. NIRS-based approaches have also been developed for other applications, including hematoma detection. The depth of tissue interrogation is typically limited to approximately 2 cm below the surface.

Functional Near-Infrared Spectroscopy (fNIRS).

fNIRS technology uses the basic principles of NIRS to evaluate temporal and spatial variations in blood content and oxygenation in response to functional biological processes. The most common applications of fNIRS are in neurological diagnostics, where variations in signals may be correlated with cerebral metabolic processes that cause changes in local Hb concentration and oxygenation levels (see, e.g., Hillman, J Biomed Opt, 12(5), 2007).

Diffuse Reflectance Spectroscopy (DRS)

DRS is similar to NIRS, but performed in the ultraviolet to visible spectral range where tissue absorption and scattering levels are much greater and penetration depth is on the order of hundreds of microns (see, e.g., Chromophore based analyses of steady-state diffuse reflectance spectroscopy: current status and perspectives for clinical adoption. T M Bydlon, R Nachabé, N Ramanujam et al., J Biophotonics 8:1-2, p. 9-24, 2015). DRS approaches have been used to measure oxygen saturation, assess metabolism, or detect cancer based on endogenous signals or exogenous contrast agents like nanoparticles using molecular imaging techniques.

Fluorescence Spectroscopy

Fluorescence spectroscopy is distinct from reflectance in that it involves the absorption of photons at one wavelength, followed by non-radiative decay in molecular energy level, and subsequent emission of longer wavelength (lower energy) photons. Fluorescence emission occurs at much lower levels of intensity than the absorbed radiation (see, e.g., Fluorescence spectroscopy of neoplastic and non-neoplastic tissues N Ramanujam—Neoplasia, 2000). Fluorescence due to endogenous tissue components is strongest at UV and visible wavelengths (due to fluorophores such as tryptophan, NADH, collagen and porphyrins), whereas exogenous fluorescence typically involves dyes, nanoparticles such as quantum dots, or proteins (produced by tissue via genetic modifications) that absorb and emit at long visible and near-infrared wavelengths.

Raman Spectroscopy

Biomedical systems for detecting Raman scattering signals typically involve illumination at a wavelength in the near-infrared and detection of light at a range of longer wavelengths (see, e.g., Raman spectroscopy of biological tissues Z Movasaghi, S Rehman, I U Rehman—Applied Spectroscopy 42:5: 493-541 2007). While Raman signals tend to be produced at much lower intensity yields than fluorescence, they enable measurement of highly specific spectral signatures of biological molecules and contrast agents.

Narrow Band Imaging.

Narrow band imaging (NBI) systems typically consist of an endoscope system and a source of light capable of delivering light within narrow spectral bands. In particular, light in violet and green regions of the visible spectrum—where Hb exhibits strong absorption peaks—are used to enhance detection of blood vessels. These devices often use a xenon lamp and bandpass or long and short-pass filters, although lasers or light emitting diode sources may provide similar optical characteristics. (see, e.g., Machida, "Narrow-band imaging in the diagnosis of colorectal mucosal lesions: A pilot study", Endoscopy, 36, 1-5, 2004).

Spectral/Hyperspectral Reflectance Imaging (HRI).

HRI is a superficial imaging technique where a camera/filter system acquires superficial images of tissues at a large number of individual consecutive narrow spectral bands, thus acquiring a full optical spectrum at each pixel in the image. Approaches involving only a few selected bands is typically referred to as spectral imaging. Spectral imaging data can be used to determine tissue absorption and scattering properties, especially relative concentrations of oxy- and deoxy-hemoglobin, as well as exogenously delivered contrast agents (e.g. ICG) (Lu et al., J Biomed Opt, 19(1), 2014). It should also be noted, that other optical signals, such as fluorescence, can also be detected with hyperspectral approaches.

Spatial Frequency Domain Imaging (SFDI).

SFDI is a form of diffuse imaging involving spatially varying illumination intensity across the tissue surface in order to enable depth-selective measurements. Reflectance-based versions are capable of estimating chromophore distributions (see, e.g., Modulated imaging: quantitative analysis and tomography of turbid media in the spatial-frequency domain. D J Cuccia, F Bevilacqua, A J Durkin, B J Tromberg—Opt. Lett, Vol. 30, Issue 11, pp. 1354-1356, 2005), whereas other forms of SFDI may provide information on other optical characteristics of endogenous or exogenous tissue biomarkers—such as fluorescence properties.

Fluorescence/Luminescence Imaging (UV-Vis, NIR)

Imaging of fluorescence from either endogenous constituents or exogenous contrast agents has been used for cancer detection as well as other applications (see, e.g., In vivo fluorescence imaging for tissue diagnostics. S Andersson-Engels et al. Phys Med Biol, 42:5, 815-824, 1997). Luminescence signals of endogenous or exogenous constituents can also be detected using imaging approaches.

Optical Coherence Tomography.

Optical coherence tomography (OCT) is based on principles of laser interferometry in a manner analogous to ultrasound imaging (see, e.g., Optical coherence tomography-principles and applications, A F Fercher et al.—Reports on Progress in Physics 66, 239-303, 2003). OCT provides non- or minimally-invasive imaging primarily based on the backscattering properties of biological tissue and/or exogenous contrast agents. The dramatic technological advances in the field of optical coherence tomography (OCT) imaging have driven commercialization and clinical adoption in ophthalmology, cardiology and gastrointestinal cancer screening.

Confocal Microscopy.

Confocal microscopy is an approach that enables high resolution, depth-sectioned images by adding a spatial pinhole at the confocal plane of the lens of a microscope to remove out-of-focus light. It can be used to generate three-dimensional image reconstructions of tissue by accumulating groups of images at different depths called optical sectioning to a depth on the order of a few hundred microns. The confocal microscopy technique has been broadly used in life sciences and materials science (see, e.g., J. B. Pawley et al., Handbook of Biological Confocal Microscopy, Second Edition, Reviewer Opt. Eng. 35(9), 2765-2766, 1996). Confocal approaches can be used to image reflectance or fluorescence signals generated in tissue.

Nonlinear Microscopy.

Techniques such as multi-photon (esp. 2-photon) microscopy have emerged over the past decade as methods for improving the imaging depth and resolution of fluorescence confocal microscopy approaches. (see, e.g., Multiphoton microscopy of endogenous fluorescence differentiates normal, precancerous, and cancerous squamous epithelial tissues. M C Skala, et al., Cancer research, 5; 65: 1180-1186, 2005.) These techniques enhance endogenous and exogenous fluorescence signals to provide information on tissues and cells relevant to diseases such as cancer.

Optical Tomography.

Diffuse Optical Tomography (DOT) is a pure optical imaging modality that offers deeper imaging (~3-4 cm) but with poor resolution (~5 mm). Light is delivered from and collected at multiple points across the tissue using fiberoptics. Many systems use endogenous tissue contrast from blood, water, and lipids. DOT has been studied extensively for breast cancer detection due to its ability to detection deep lesions with different optical properties from adjacent healthy tissue. Recently, a combined DOT/PAT system has been demonstrated, where DOT data is used to improve the quality of PAT measurements of quantitative chromophore concentration and distribution (Li et al., Biomed Opt Express, 2(8), 2348-2353, 2011). Other versions of optical tomography have been developed that involve detection of fluorescence or luminescence emitted by introduced contrast agents (Ntziachristos et al., PNAS, 97(6), 2767-2772, 2000) such as proteins (e.g., GFP) or dyes. These approaches are increasingly used in commercially available small animal imaging systems to detect biomarkers in tissue for research studies, such as preclinical pharmaceutical/medication/treatment effectiveness investigations.

Multi-Modal Diagnostics—Photoacoustic Systems

In recent years there has been increasing interest in combing optical approaches with other medical imaging technologies to develop new multi-modal devices with advanced capabilities. One of the most promising areas that has emerged from these efforts is photoacoustics (also known as "optoacoustics"). Photoacoustics is an emerging field with a rapidly increasing range of clinical imaging and sensing applications. By irradiating tissues with pulsed light, thermoacoustic waves are generated in absorptive tissue regions, which can be collected by acoustic transducers. By varying the optical wavelength (Photoacoustic Spectroscopy), multispectral data can be used to sense and isolate absorption features of different tissue components. Use of a single stationary transducer results in a photoacoustic sensor device, where the received acoustic signal is correlated to tissue light absorption. By mechanically or electronically scanning one or more transducers, an image can be produced, giving rise to PAI. Due to high absorption of Hb in blood, vasculature can be imaged noninvasively at depths of 4-6 centimeters (Wang and Hu, Science, 335(6075), 1458-1462, 2012), much deeper than the penetration depth of any commercial optical imaging system based on light transport alone. Thus, PAI can provide information on optical absorption contrast—which pure ultrasound cannot provide—at greater depths than pure optical imaging. One key application of PAI using endogenous contrast is cancer detection based on angiogenesis, especially for mammography. Exogenous contrast agents (e.g., dyes, nanoparticles) may also be administered for applications such as cancer detection and lymph flow imaging.

Generally, PAI systems are classified into two types: Photoacoustic Computed Tomography (PAT) and Photoacoustic Microscopy (PAM) (Wang and Hu, Science, 335 (6075), 1458-1462, 2012). PAT is well-suited for macro-scale imaging over wide fields of view to depths of 4-5 cm, while PAM is capable of performing microscopic imaging of small blood vessel networks in shallow tissues (~1-5 mm depths). One clinical application of PAT is mammography, since deep penetration is required to interrogate breast lesions. Many PAT mammography systems utilize a standard clinical ultrasound system and linear array transducer to collect acoustic signals. In addition to systems designed for imaging breast and other large organs, there are many examples of intravascular or endoscopic PAI systems, such as systems for vascular plaque detection (Wang et al., Sci Rep-Uk, 4, 2014). PAM systems often resemble a benchtop microscope. Light is focused to a very small spot size, and a focused acoustic transducer is used to collect signals from a smaller region of tissue. PAM systems may be limited by either the optical resolution or acoustic resolution. While PAM offers penetration depths of 1-10 mm (much deeper than pure optical microscopy), it also offers high spatial resolution (~1-10 µm lateral, 5-15 µm with depth). By imaging at multiple wavelengths, highly detailed maps of vasculature can be generated with spectral information related to vessel oxygenation. The disclosed phantoms can be readily constructed for PAM applications.

Performance Characteristics of Detection Systems for Tissue Interrogation

The disclosed phantoms can be used to calibrate and assay numerous performance characteristics of an optical detection system, such as a NIRS system, or any system that generates optical data and can benefit from a phantom having biomimetic optical properties (for example, NIRS imaging data). Non-limiting examples of such performance characteristics are provided below:

Hb Saturation Measurement Accuracy.

Many imaging and spectroscopy systems are designed to measure absolute Hb saturation values or relative changes in Hb saturation as a function of position or time. The ability to objectively, quantitatively evaluate the ability of these systems to measure bulk hemoglobin saturation values or local values (e.g, in specific blood vessels) is critical. Phantoms that incorporate Hb with known saturation levels—or contain inclusions with known saturation levels—can be used to evaluate saturation measurement accuracy and/or the ability to evaluate spatial or temporal variations in Hb saturation.

Hb Concentration Measurement Accuracy.

Similarly as with Hb saturation, many optical imaging and spectroscopy devices measure Hb concentration or changes in concentration with time or position. Thus, phantoms with different concentrations, or with fixed inclusions that contain known concentrations of Hb (or with empty inclusion spaces to accommodate removable inclusions with known concentrations of Hb), can be used to provide objective, quantitative assessment Hb concentration measurement accuracy.

Low Contrast Detectability/Contrast-Detail Analysis.

Angiogenesis is a well-known component of carcinogenesis. The ability to detect regions of high vascularity can, in the case of many optical imaging systems enable early detection of cancer. Therefore, phantoms that incorporate inclusions of different sizes and Hb concentration can be used to evaluate a device's ability to detect regions of enhanced vascularity that may be indicative of neoplasia. Evaluation of how detectability varies with Hb concentration and lesion size can be evaluated qualitatively or quantitatively with Hb-inclusion phantoms.

Spatial Resolution (Axial, Lateral, Elevational):

The ability to distinguish two adjacent objects from each other. Spatial resolution in imaging can be measured using many different phantom targets. A single thin wire or filament may be imaged over its cross section, producing a resolution-limited point spread function (PSF) from which axial and lateral resolution may be calculated. Alternatively, images may be acquired along the wire axis, showing a line spread function (LSF). In some embodiments, the phantom can contain dense arrays of adjacent wires, relying on visual distinction of overlapping PSFs as the measure of resolution. Targets for resolution testing should be much smaller than the resolution of the system (e.g. <100 µm for a typical PAT system).

Penetration Depth:

The maximum depth at which a target of known absorbing strength is detectable. This characteristic may be tested using an array of equally absorptive targets at several depths within the phantom. If the detection criterion is qualitative visualization by an observer, the maximum penetration depth is given by the deepest visualized target. Quantitative analysis may also be used, where metrics such as target contrast, contrast-to-noise ratio, or signal-to-noise ratio above a certain threshold may dictate sufficient detectability.

Low-Contrast Detectability, Contrast-Detail Analysis:

Visualization of a target depends on its intensity/brightness as well as its size and shape (e.g. a small but medium-contrast target may be more visible than a large but low-contrast target). Testing of this effect is referred to as contrast detail analysis; contrast detail analysis phantoms possess targets of varying size at different contrast levels. Low-contrast detectability, the ability to visualize weak-signal targets against background signals, is a related component of this analysis that captures the sensitivity of the system to target absorption strength (related to concentration of absorbing particles/chromophores).

Field of View (FOV):

The physical dimensions of the area or volume that may be simultaneously imaged by a system. FOV tests may be performed in phantoms with any type of target, but small, high-contrast targets provide the most accurate determination of FOV.

Uniformity:

Image intensity may vary within the FOV due to many factors, e.g. uneven illumination of the tissue, differences in tissue optical/acoustic properties, or reconstruction artifacts. To distinguish from target contrast variance with depth (see Penetration Depth and Low-contrast detectability), uniformity can be defined as the image background uniformity. Uniformity may be tested in a phantom similar to penetration depth phantoms, where an expected depth dependence in background signal may be observed and quantified.

Distortion:

Distortion is the spatial warping of an image resulting in deviation of perceived physical dimensions from the true physical dimensions. Distortion may result from hardware effects (e.g. optical lensing/focusing, acoustic transducer aperture effects) or inadequate image reconstruction (e.g. incorrect assumed speed of sound in the phantom causes mis-registration of spatial coordinates). Distortion may be quantified using an array of targets with known spacing in a regular pattern within the image (e.g. rectangular grid of sub-resolution targets or larger targets). The choice of target depends on what distortion sources are of interest: geometric distortion/mis-registration is easily captured using point targets, while other types of distortion such as reconstruction artifacts should be characterized using larger targets.

Spatial Measurement Accuracy:

Spatial measurement accuracy is another component of spatial registration accuracy (see Distortion), referring to measurement of distances, areas, and volumes of features within the image. Distance accuracy is the simplest type of spatial measurement, and may be readily characterized using sub-resolution PSF targets placed at highly accurate positions within a phantom with biologically relevant optical and acoustic properties (IEC 61391-1 calls for placement to within +/−0.1 mm). Because tissues are heterogeneous, interfaces with mismatched acoustic properties cause reflection artifacts and spatial mis-registration. The disclosed biophotonic phantoms may be used to simulate these complex tissue environments, where traditional PAT/ultrasound phantoms are acoustically uniform.

Signal-to-Noise Ratio (SNR):

SNR is a description of the recoverability of a target signal relative to the noise/image background, but generally refers to the measured wavelength amplitude of the detected signal, rather than the SNR of the imaged target based on pixel intensity. SNR may be characterized vs. depth (see penetration depth) using an array of absorptive inclusions. However, instead of computing target contrast relative to the background, target intensity is compared against an image acquired under pure electronic noise (e.g., the transducer in open air).

Linearity:

Linearity describes the relationship between target signal strength and its imaged intensity. Linearity may be measured using similar phantoms to low-contrast detectability, such as an array of targets with different known signal strength. Linearity is determined by curve-fitting measured target image intensity versus target absorption strength (e.g. contrast level or absorber concentration). Linearity may be affected by system hardware and software as well as by tissue effects. Linearity phantoms may be comprised of one or more channels filled with varying concentrations of an absorptive dye/material, where images are recorded for each concentration and target intensity/contrast data are compared. Linearity can also be represented as the relationship between a secondary parameter (e.g., blood oxygenation, pH)—that causes changes in a detectable parameter (e.g., absorption coefficient)—and the imaged or device-detected intensity.

Dynamic Range:

The range of device-determined signal intensities that can be generated based on a range of inherent target strengths—ideally from a target strength of zero to the maximum expected in biological tissue. It can also be represented as the range of device-generated signal intensities caused by changes in a secondary parameter (e.g., temperature, pH), that directly affects a detectable parameter (e.g., absorption coefficient).

Artifacts:

Artifacts are undesirable features in an image that do not represent the structure or properties of the sample being imaged or measured. The presence of artifacts may degrade image/data quality and/or obfuscate visualized features in an image, making image/data interpretation challenging. Artifacts may be caused by incorrect acquisition and post-processing techniques, as well as by tissue/sample properties and geometry, instrumentation or physical processes which cannot easily be corrected for by data processing, or some combination of these factors. System susceptibility to artifacts may be characterized using phantoms containing inclusions designed to reproduce artifacts encountered in tissue. Artifacts may be quantified using metrics such as artifact-to-noise ratio or artifact-to-background ratio.

Spectral Measurement Accuracy:

Optical imaging techniques may utilize multiple-wavelength illumination to perform spectroscopic measurement of tissues. The measured spectra may be thought of as a combination of the spectra of distinct chromophore species (e.g. water, lipids, blood, nanoparticles). From these spectral data, unmixing algorithms may be used to determine the relative amount of each absorber present. Phantom methods for evaluating this aspect of such systems should provide targets and a background medium with biologically relevant optical property spectra. For example, hemoglobin solutions contained within fluid channels will accurately simulate discrete blood vessel absorption at multiple wavelengths, while phantom background properties could be tuned to match tissue-relevant absorption and scattering spectra. Specific versions of this testing include evaluation of:

a. Tissue blood oxygenation ($SO_2$) due to oxy-, deoxy-hemoglobin b. Concentration of dyshemoglobins (metHb, carboxyHb)

c. Concentration of targeted or untargeted contrast agents (plasmonic nanoparticles, absorptive or fluorescent dyes).

Biomimetic Geometry:

One of the advantages of the disclosed phantoms is that they can be formed into the shape of living organ or tissue, of body parts, or of whole animals (such as a small mammal, for example a mouse), and can further include selected defects, such as optical or acoustic inclusions. Thus, the disclosed phantoms can be used to test and calibrate the performance of optical detection systems in the context of a sample with a morphologically realistic shape.

EXAMPLES

The following examples are provided to illustrate particular features of certain embodiments, but the scope of the claims should not be limited to those features exemplified.

Example 1

Solid Hemoglobin-Polymer Phantoms for Evaluation of Biophotonic Systems

This example describes development and validation of a novel polymer material incorporating hemoglobin. The solid hemoglobin-polymer (SHP) material is fabricated by mixing liquid silicone base with a hemoglobin solution, followed by sonication and low temperature curing. The optical properties of samples were determined over the 450-1000 nm using the Inverse Adding-Doubling method and the Beer-Lambert law. Measurements indicated SHP optical stability over four months. Near-infrared spectroscopy and HRI measurements of SHP samples were performed to demonstrate the utility of this approach. SHP materials have the potential to improve tissue-simulating phantoms used for development, evaluation, and standardization of optical devices for oximetry and other applications.

Hb is perhaps the most important chromophore for many biophotonic diagnostic techniques such as NIR spectroscopy, HRI, and photoacoustic imaging. In these approaches, Hb can act as a biomarker or indicator of tissue health. In other techniques, such as fluorescence spectroscopy, Hb absorption represents a key source of interference that must be avoided or extracted. As a result, Hb is often a key component in tissue-simulating phantoms used to elucidate light-tissue interactions, evaluate device working mechanisms and performance during preclinical development, as well as provide standardization and recalibration during in vivo studies or clinical use.

Constructing phantoms that mimic the optical signatures of oxy- and deoxy-Hb over a wide spectral range has been a significant challenge for researchers. Prior phantom designs have either incorporated Hb solutions (Durkin, et al. Appl. Spectroscopy 47, 2114, 1993) or combinations of dyes (Akl, et al. Biomed. Opt. Express 2, 2096, 2011) to simulate the optical effects of blood in tissue. However, liquid phantoms containing Hb suffer from drawbacks including a lack of stability due to evaporation and settling of suspended components, difficulty in incorporation of inhomogeneous structures such as multiple layers or vascular structures, as well as an inability to maintain Hb saturation levels over long periods of time (Li, et al. Sci. Rep. 3, 1358, 2013;

Kurth, et al. Phys. Med. Biol. 40, 2079, 1995). Hydrogel phantoms can have arbitrary desired shapes but they are fragile and shapes changed due to evaporation (Pogue, et al. J. Biomed. Opt. 11, 041102 (2006)). In addition, approaches involving combinations of non-biological dyes are limited to small spectral and dynamic ranges (Akl, et al. Biomed. Opt. Express 2, 2096, 2011) or have short-term stability limited to a few days or weeks (Pekar, et al. Med. Laser Appl. 25, 147, 2010). Solid polymer phantoms can be a solution to achieve long term stability, robustness to handling, and flexibility in fabrication (Pogue, et al. J. Biomed. Opt. 11, 041102, 2006), however, compatibility between biological materials such as Hb and polymers and the methods (e.g., heating) used for curing typically represents a significant challenge. Therefore, a stable material that incorporates the spectral features of oxy-Hb and/or deoxy-Hb absorption and can be incorporated into tissue phantoms would be of widespread interest and utility.

This example provides, for the first time, a method to fabricate solid Hb-polymer (SHP) materials that exhibit the spectral absorption characteristics of Hb and have long-term optical stability. Optimal approaches for mixing and curing SHP materials are provided, as is data showing measurements of optical properties across the visible and NIR range at regular intervals for a period of up to one year. Practical demonstrations involving measurements with NIR spectroscopy and HRI systems are also disclosed.

An embodiment of the SHP fabrication process is outlined in FIG. 1. Initially, a mixture of Polydimethylsiloxane (PDMS) and purified human Hb solution (Level 2, Multi-4 Co-Oximetry controls, Instrumentation Laboratory Co., Bedford, Mass.) was prepared. The latter is fully oxygenated and has a normal human Hb concentration level (150 g/liter) (Bosschaart, et al. Lasers Med. Sci. 29, 453 (2014)). A liquid-form silicone, PDMS (Sylgard® 184 Silicone Elastomer, Dow Corning, Midland, Mich.), is used as a base matrix material. Approaches involving mixtures of silicone with water-based dyes or blood products previously generated little interest because a liquid silicone base is difficult to mix homogeneously with an aqueous solution due to its high hydrophobicity. To overcome this issue, a carefully monitored sonication process was employed.

An oxy-Hb SHP material was prepared at a 1.8% Hb concentration by mixing 0.6 g of Hb stock solution (150 g Hb/liter), 4 g of PDMS, and 0.4 g of PDMS curing agent. The concentration of Hb stock solution in the oxy-Hb phantom was set to 12% of the total weight of the Hb-PDMS mixture in the phantom to obtain enough transmission light in visible and NIR regions. This type of dilution is a broadly used approach in spectroscopic measurement of optical properties (Bosschaart, et al. Lasers Med. Sci. 29, 453, 2014; Wagnières, et al. Phys. Med. Biol. 42, 1415, 1997). The standardized Hb solution and PDMS solution were then mixed using a sonicator (Qsonica, Newton, Conn.) with a pulsed on/off setting of 3 sec/37 sec at an amplitude of 20% for 10 hours. The mixture was homogeneously distributed after the sonication process and its viscosity was increased. The PDMS curing agent (hardener) was added to the mixture at a mass ratio of 10:1 (PDMS:hardener) and was stirred until uniform for 5 minutes. An aluminum disk PDMS mold (1.5 inch diameter, 3 mm thickness) was created, placed in a petri dish, and PDMS was poured on the disk. The mold was placed in a vacuum chamber for approximately one hour to extract bubbles generated by the mixing process and then cured on a hot plate for one hour at 50° C. After removing the mold, the empty cavity produced by the mold was filled with the Hb-PDMS mixture. Phantoms of various thicknesses can be produced using the mold. To fabricate a deoxy-Hb phantom, yeast powder was dissolved in distilled water (mass ratio of 1:2) and added to the Hb-PDMS mixture. The deoxy-Hb phantom was fabricated by adding 0.2 g of yeast to the prepared oxy-Hb-PDMS mixture for deoxygenation. The mixture was placed in vacuum for 6 hours to remove dissolved air. It was then poured into the PDMS mold. Another layer of PDMS was used to cover the top so that the Hb-PDMS mixture was completely encapsulated by PDMS. No diffusion between layers was observed. The phantom was fully solidified after curing at room temperature for 1-2 days. PDMS is capable of rapid curing at higher temperatures, however, the process involves room temperature curing to avoid thermal effects on Hb (e.g., denaturation, oxidation).

PDMS was selected as the base material for the phantom because of its various merits. It has a low intrinsic $\mu_a$ in visible and NIR spectral regions and a refractive index of ~1.4 (Long, et al. Biomed. Opt. Express 2, 1877, 2011), which is in the tissue-relevant range. Due to the deformability of PDMS, cured PDMS phantoms are more biologically realistic for contact-based optical methods compared to other rigid materials such as polyurethane and polyester (Firbank, et al. Phys. Med. Biol. 38, 847, 1993).

Three oxy-Hb and three deoxy-Hb SHP samples were fabricated to investigate their optical properties and stability. Each sample was fabricated on a different day and from a different vial of the Hb solution. After fabrication, the phantoms were sealed in plastic bags filled with $N_2$ gas to prevent gas permeation and stored in a refrigerator at 4° C. between measurements. $\mu_a$ and $\mu_t$ were measured for all samples at intervals of 2 or 3 weeks. For $\mu_a$ measurements, transmittance and diffuse reflectance were measured by a dual-beam spectrophotometer (Perkin Elmer Lamda 1050, Waltham, Mass.) that incorporates Tungsten-Halogen and Deuterium lamps and an integrating sphere (150 mm diameter, Labsphere, Perkin Elmer, Waltham, Mass.). To obtain the absorption of phantoms in the NIR region, we used the well-established inverse adding doubling (IAD) method (Prahl. Oregon Medical Laser Center 4, 1998). However, in the visible region, the measured reflectance values were too low for IAD to successfully converge and provide a $\mu_a$ and a reduced scattering coefficient ($\mu_s'$). Therefore, the Beer-Lambert law was used to calculate the $\mu_t$ in the visible region.

SHP sample optical spectra at various time points after fabrication are shown for oxy-Hb in FIG. 2. Key features are clearly seen in visible wavelengths (FIG. 2A), including strong peaks at 540 nm and 575 nm, which are characteristic of oxy-Hb absorption (Bosschaart, et al. Lasers Med. Sci. 29, 453, 2014). In the NIR data shown in FIG. 2B, the valley around 700 nm and the broad peak from 700 nm to 1000 nm closely match with the reference $\mu_a$ (Prahl, et al. Appl. Opt. 32, 559, 1993). Standard deviations at three selected wavelength regions, which represent main absorption features, are shown in FIG. 2. The reference absorption spectrum of Hb (Prahl, et al. Appl. Opt. 32, 559, 1993) rescaled to 1.8% human blood content is shown for comparison in FIG. 2. Two potentially undesirable characteristics seen in the SHP sample results are: (1) the absorption peak near 910 nm, which is not attributable to Hb, rather a common absorption feature of PDMS (Cal, et al. J. Mol. Struct. 976, 274, 2010), and (2) the excess absorption of about 1 $cm^{-1}$ seen across the NIR region. The latter feature may introduce some limitations in the application of SHP-based phantoms for NIR applications, however, it may also provide a useful bulk approximation of background tissue chromophores. To measure the absorption of PDMS, a sample was created that matched the size of the phantoms and its absorption using the spectrophotometer was measured. These features are also noted in the deoxy-Hb samples.

The three deoxy-Hb SHP samples were evaluated in a similar manner as the oxy-Hb samples. Several typical features of deoxy-Hb in the visible and NIR ranges are shown in FIG. 3. A single strong peak near 550 nm, a small peak near 750 nm, and a flat feature from 800 nm to 1000 nm were observed, all of which are in good agreement with well-known features of deoxy-Hb absorption (Prahl, et al. *Appl. Opt.* 32, 559, 1993). Standard deviations at these particular wavelengths are also shown in FIG. 3.

Figure 4B:
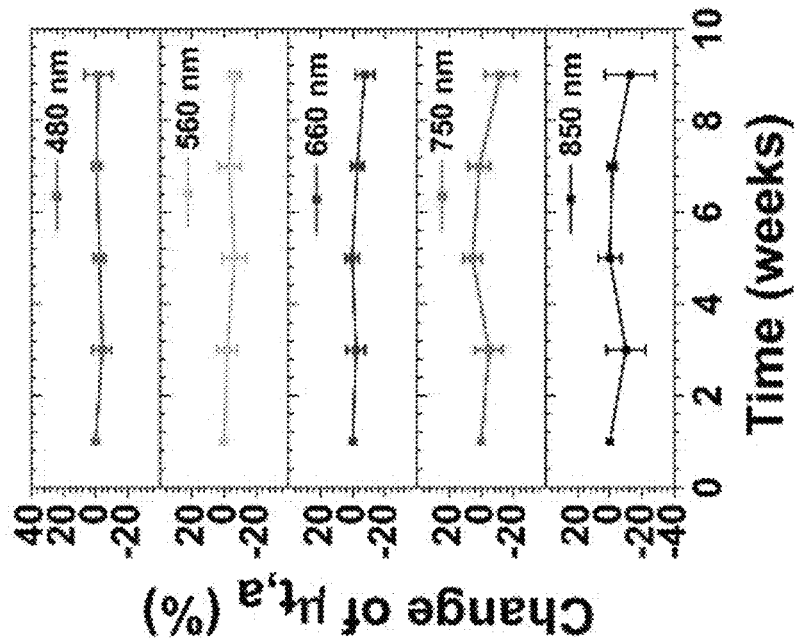
FIGS. 4A and 4B are a set of graphs showing the relative stability of oxygenated-Hb (FIG. 4A) and deoxygenated-Hb (FIG. 4B) samples at five selected wavelengths of interest.
Figure 4A:
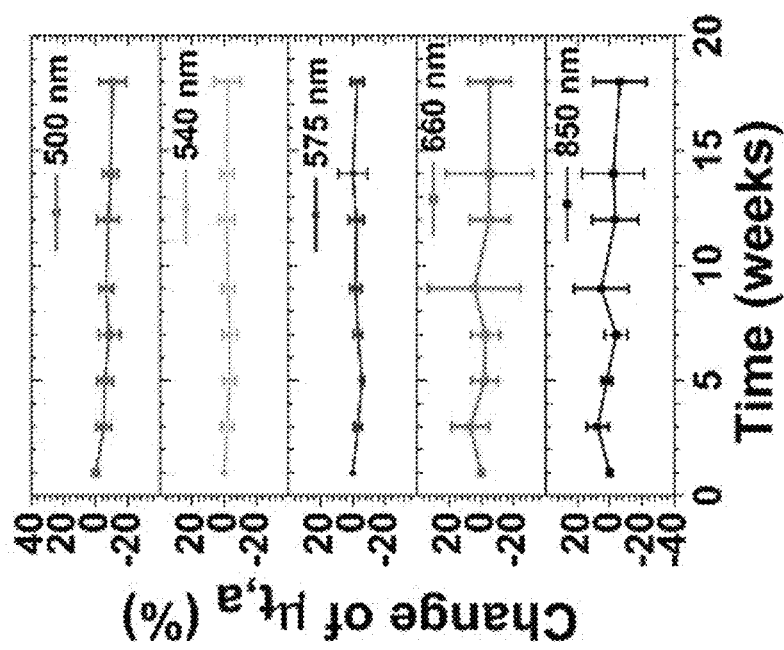

To evaluate the changes in $\mu_t$ and $\mu_a$ over time, measurements taken at regular intervals were compared to the initial value at each of the selected five different wavelengths as shown in FIG. 4. A moderate degree of experimental variability (up to ~20%) was observed, however, no significant trend in $\mu_t$ or $\mu_a$ was seen over four months for the oxy-Hb samples and nine weeks for the deoxy-Hb samples. In addition, the $\mu_s'$ in the NIR region was calculated using IAD, which was found to be nearly constant across NIR wavelengths. Mean $\mu_s'$ values of oxy-Hb phantoms were 2.6 (±0.3) cm$^{-1}$ at 650 nm, 2.4 (±0.3) cm$^{-1}$ at 800 nm, and 2.6 (±0.3) cm$^{-1}$ at 950 nm. Mean $\mu_s'$ values for deoxy-Hb phantoms were 3.9 (±0.1) cm$^{-1}$ at 650 nm, 4.0 (±0.1) cm$^{-1}$ at 800 nm, and 3.7 (±0.1) cm$^{-1}$ at 950 nm.

Figure 5A:
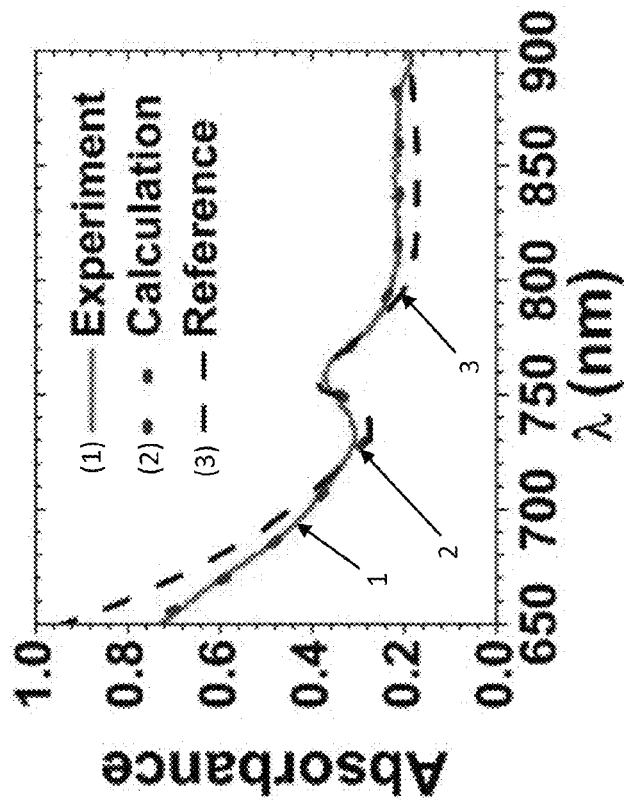
FIGS. 5A and 5B are a set of graphs showing a comparison of measured near-infrared spectroscopy (NIRS) results with data calculated from the unmixing algorithm based on (FIG. 5A) oxygenated-Hb silicone (PDMS) and (FIG. 5B) deoxygenated-Hb silicone (PDMS) phantoms. For comparison, the dashed line shows data based on 1.8% Hb (12% Hb stock solution) (Prahl, et al. Appl. Opt. 32, 559, 1993) concentration in the solid Hb phantom.
Figure 5B:
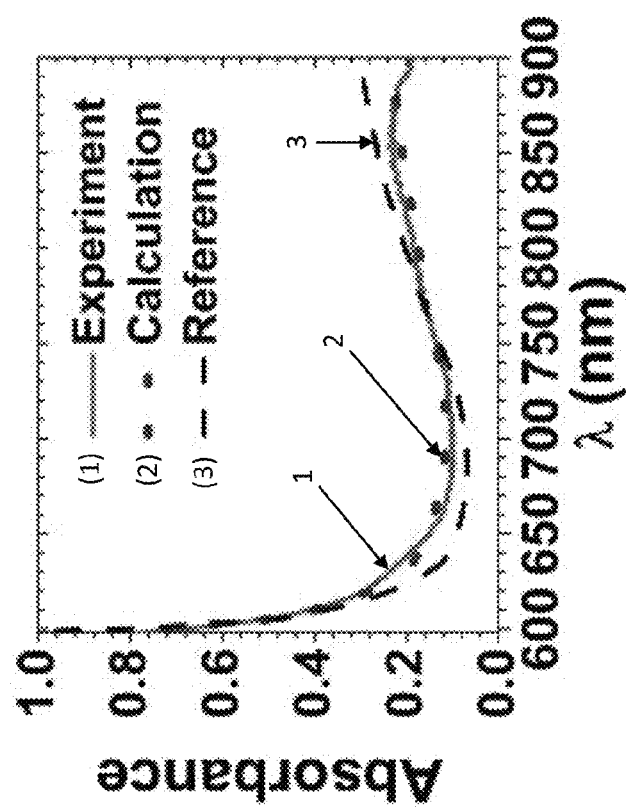

Additional practical testing was performed to assess the utility of SHP-based phantoms. This involved performing measurements with a fiberoptic-probe-based NIRS system—based on a Xenon light source and linear array spectrometer—and a turbid polyoxymethylene (POM) phantom (Jang, et al. *Proc. SPIE BiOS*, 9315, 931503, 2015). The cylindrical POM matrix contained a 2 mm path length cuvette (Jang, et al. *Proc. SPIE BiOS*, 9315, 931503, 2015) made of POM that was filled with SHP material at 1.8% Hb by weight (12% Hb stock solution by weight) concentration for these measurements. Absorbance results using the NIRS system are shown in FIG. 5. In the NIR region, we observed typical oxy-Hb (FIG. 5A) and deoxy-Hb (FIG. 5B) absorbance.

The oxygenation levels were estimated from NIRS data by performing spectral unmixing with a nonlinear least squares algorithm (Matlab®, The Mathworks, Inc.) (Lawson, et al. *Solving least squares problems* (Prentice Hall, 1974)):

$$\text{Min} \|\varepsilon * C - A\|^2 \quad (1)$$

where $\varepsilon$ is the known molar extinction coefficient, C is the concentration, and A is the absorption spectra from the NIRS system. Here it was assumed that the spectrum measured by the NIRS system is a linear summation of each chromophore where the amount of each chromophore is nonnegative. For calculation of the relative contribution of each component, the known absorption spectra of oxy-Hb and deoxy-Hb were used (Prahl, et al. *Appl. Opt.* 32, 559, 1993). The absorption spectra of POM and PDMS were independently measured. Oxygen saturation (SO$_2$) are computed as follows: SO$_2$=C$_{HbO2}$ (C$_{HbO2}$+C$_{Hb}$). The SO$_2$ was estimated to be 92% in the oxy-Hb phantom and 0% in the deoxy-Hb phantom. To check the reliability of this unmixing algorithm, absorbance from the obtained concentration of each component from the unmixing algorithm was retrieved and compared with the measurement results in FIG. 5. These preliminary results provide evidence that SHP materials can serve as effective tissue-simulating phantom materials for biophotonic imaging and spectroscopy devices, particularly tissue oximetry.

As another practical test of SHP-based phantoms, oxy- and deoxy-Hb SHP phantoms were imaged with an HRI system, which was developed previously (Wang, et al. *Opt. Lett.* 39, 3010, 2014). The HRI system includes a 100 W quartz tungsten-halogen light source (Oriel Instruments, Stratford, Conn.) for illumination. Light reflected from the sample was collected by a macro video zoom lens (Edmund Optics, Barrington, N.J.), delivered through a liquid crystal tunable filter (LCTF, CRI Varispec, Perkin Elmer, Waltham, Mass.) and measured by a visible-NIR CCD camera (Princeton Instruments, Trenton, N.J.). The absorption spectrum of each pixel in an image (1024×1024 pixels) was taken sequentially across a wavelength range of 650-1000 nm, with an interval of 10 nm and a field of view of 4.8 cm×4.8 cm. SO$_2$ in each pixel was calculated by applying the nonlinear least squares algorithm (Lawson, et al. *Solving least squares problems* (Prentice Hall, 1974)) to the measured absorption spectra of each pixel. Additional details regarding HRI systems and methods of calculating SO$_2$ have been previously described (see, e.g., Wang, et al. Opt. Lett. 39, 3010, 2014).

Figure 6B:
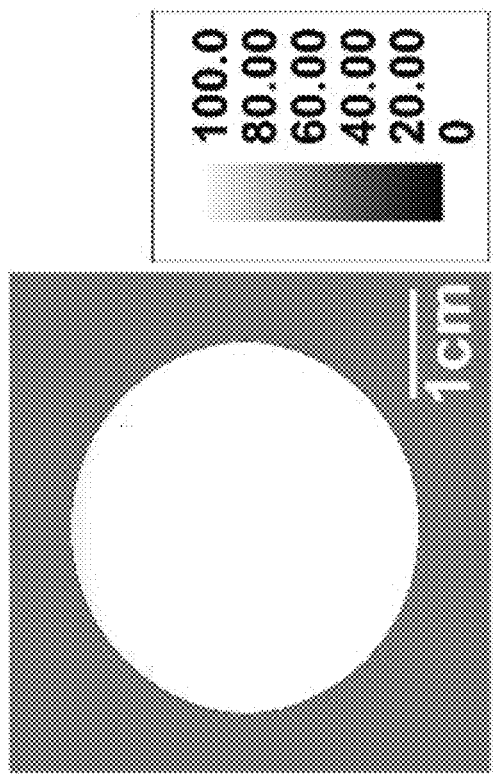
FIGS. 6A and 6B are a set of images showing HRI-measured $SO_2$ maps of (FIG. 6A) the oxygenated-Hb silicone (PDMS) phantom and (FIG. 6B) the deoxygenated-Hb silicone (PDMS) phantom.
Figure 6A:
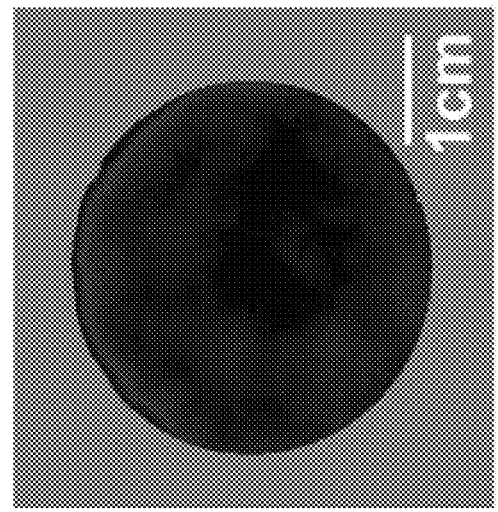

The SO$_2$ maps of one oxy- and one deoxy-Hb SHP phantoms are shown in FIG. 6. Each phantom was measured three times and the mean SO$_2$ values in the SPH material for the three measurements for each phantom were calculated. The mean SO$_2$ was 6.5±0.1% in the deoxy-Hb SHP phantom and 98%±0.1 in the oxy-Hb SHP phantom.

Figure 7:
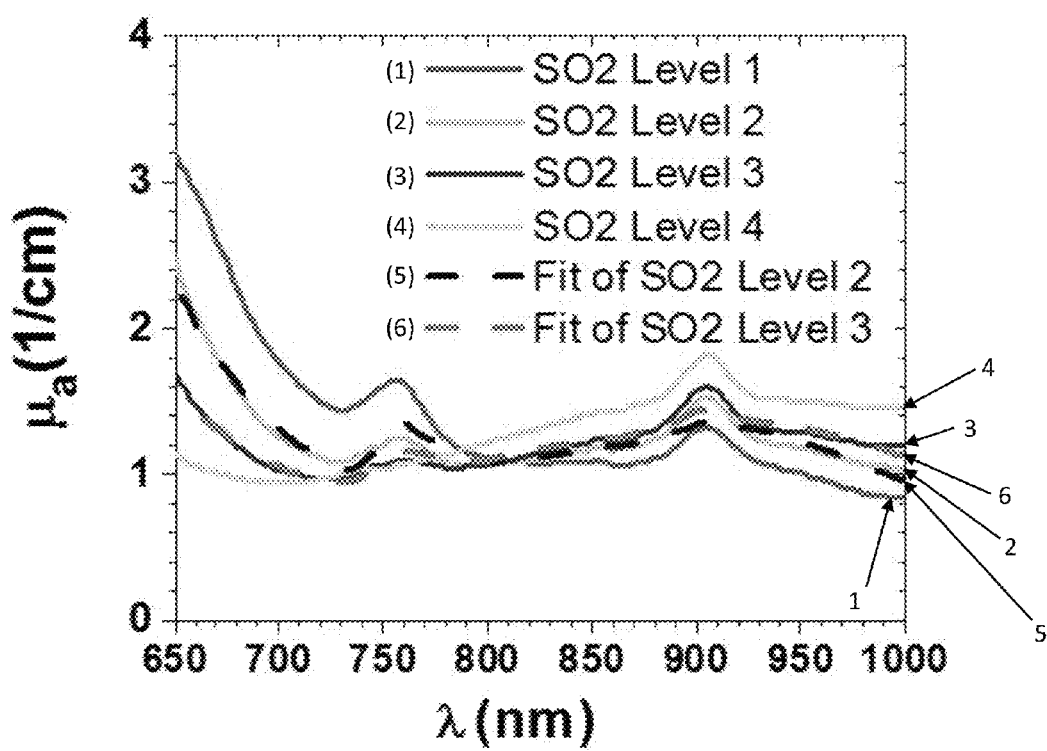
FIG. 7 is a graph showing the $\mu_a$ of Hb phantoms with varying levels of oxygenation at selected time intervals across the near infrared spectrum.

To show that an intermediate saturation level can be achieved in the disclosed biophotonic phantoms, Sodium Dithionite was added during manufacture of the solid Hb-polymer materials to create phantoms having an intermediate oxygenation level. The same process for the fabrication process of the phantoms as described above was used except for adding Sodium Dithionite instead of adding yeast. Two intermediate-saturation phantoms were made. The first phantom referred as SO$_2$ Level 2 was created by adding 160 mg of Sodium Dithionite to 4.4 g of SHP. The second phantom referred as SO$_2$ Level 3 was created by adding 80 mg of Sodium Dithionite to 4.4 g of SHP. The $\mu_a$ of the phantoms in the NIR region was calculated by using the inverse adding doubling (IAD) method. The $\mu_a$ of the phantoms are shown in FIG. 7. The unmixing algorithm (above) was applied to $\mu_a$ of the phantoms to estimate the oxygen saturation (SO$_2$). The SO$_2$ of the phantom (SO$_2$ Level 2) was 50% and the SO$_2$ of the phantom (SO2 Level 3) was 70%. To check the reliability of the unmixing algorithm, the $\mu_a$ from the obtained concentration of each component from the unmixing algorithm was retrieved and compared with the measurement results. The dashed lines in FIG. 7 show the retrieved $\mu_a$ from the unmixing algorithm for the phantoms (SO$_2$ Level 2 and SO$_2$ Level 3).

Figure 3A:
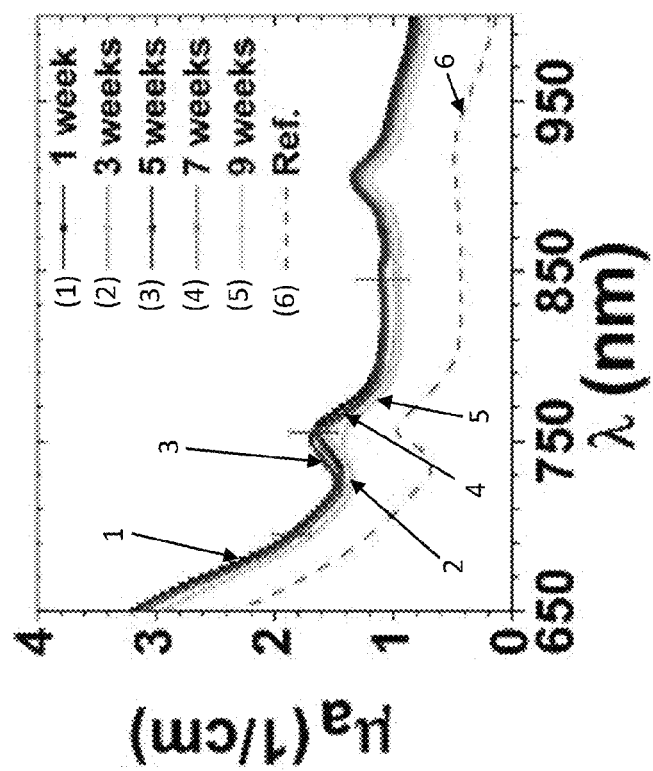
FIGS. 3A and 3B are a set of graphs showing the $\mu_t$ and $\mu_a$ of deoxygenated Hb-PDMS phantoms encased in a 4 mm shell of Hb-free PDMS at selected time intervals across the (FIG. 3A) visible and (FIG. 3B) near infrared spectral regions. $\mu_a$ measurements at visible (FIG. 3C) and near infrared (FIG. 3D) specta were also obtained one year following phantom construction. The dashed line shows reference data on human blood absorption, rescaled for dilution of the SHP sample (from Prahl et al., Appl. Opt., 32, 559 (1993)).
Figure 3B:
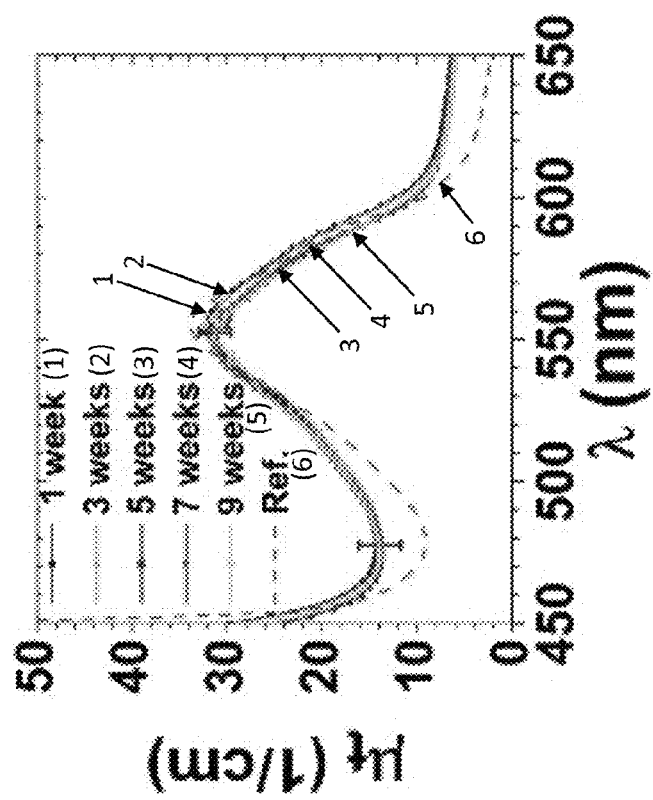
Figure 3C:
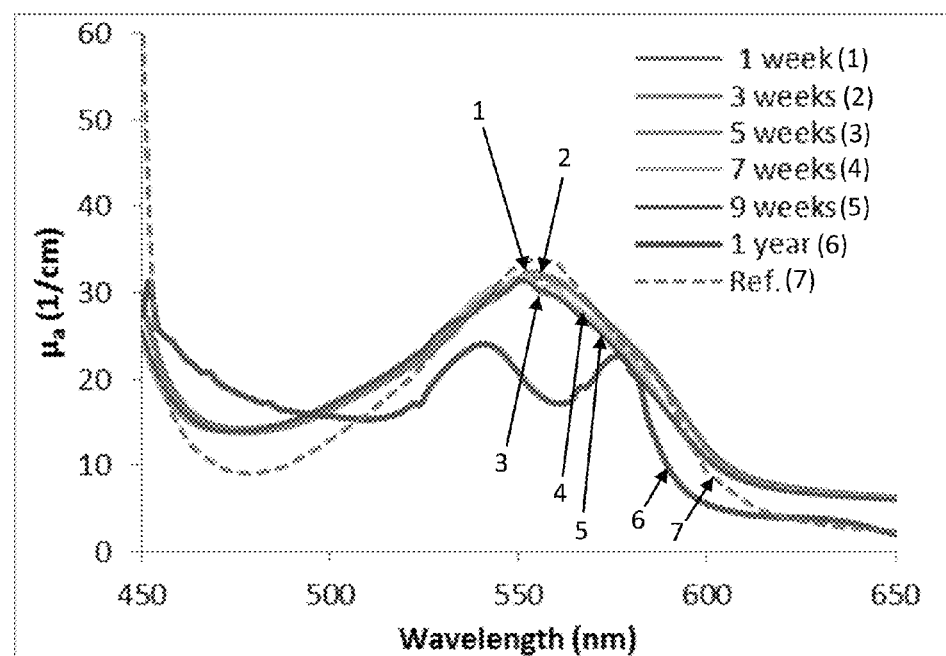
Figure 3D:
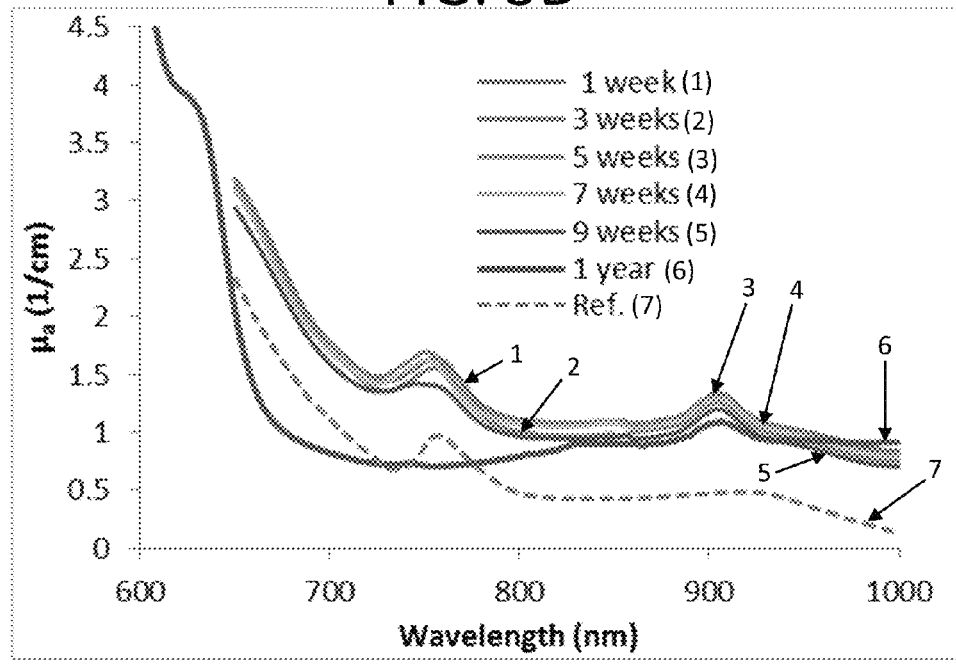

As a comparison of $\mu_a$ of the intermediate level phantoms using Sodium Dithionite, the $\mu_a$ of the complete deoxy-Hb phantom in the first week measurement in FIG. 3B was selected, which is referred as SO$_2$ Level 1. The $\mu_a$ of the complete oxy-Hb phantom in the first week measurement in FIG. 2B, which is referred as SO$_2$ Level 4. The unmixing algorithm was also used to calculate SO$_2$ from the $\mu_a$ of the phantoms. The SO$_2$ of the complete deoxy-Hb phantom (SO$_2$ Level 1) was 0% and the SO$_2$ of the complete oxy-Hb (SO$_2$ Level 4) was 100%.

As a result, the typical absorption peak of deoxy-Hb at 760 nm was increased in FIG. 7 as the concentration of Sodium Dithionite was increased. The phantoms in the intermediate oxygenation level (SO$_2$ Level 2 and SO$_2$ Level 3) show the spectral features between the complete deoxy-Hb phantom (SO$_2$ Level 1) and the complete oxy-Hb phantom (SO$_2$ Level 4).

This example describes generation of SHP phantoms exhibiting absorption spectra of oxy- and deoxy-Hb and describes a fabrication process for producing phantoms with repeatable optical properties. The results indicate that this Hb-polymer phantom approach is an effective tool for evaluating systems in which Hb absorption is a significant factor. Its main advantages are their solid spectral features of oxy- and deoxy-Hb and long-term stability. These phantom materials can facilitate standardization and performance comparison for various biophotonic technologies.

It will be apparent that the precise details of the methods or compositions described may be varied or modified without departing from the spirit of the described embodiments. We claim all such modifications and variations that fall within the scope and spirit of the claims below.

We claim:

1. A biophotonic phantom comprising a solid matrix of cured polydimethylsiloxane (PDMS) comprising distributed hemoglobin (Hb) that is in a native conformation.

2. The biophotonic phantom of claim 1, wherein the Hb is homogenously distributed in the solid matrix of cured PDMS.

3. The biophotonic phantom of claim 1, wherein the solid matrix of cured PDMS comprising distributed Hb comprises an attenuation coefficient and an absorption coefficient that remain stable across visible and/or near infrared wavelengths for at least two months following curing of the PDMS in the matrix.

4. The biophotonic phantom of claim 3, wherein the attenuation coefficient and the absorption coefficient change no more than 10% for at least two months following curing of the PDMS in the matrix.

5. The biophotonic phantom of claim 3, wherein the attenuation coefficient and the absorption coefficient of the solid matrix of cured PDMS comprising distributed Hb remain stable across 400-1000 nm light for at least two month following curing of the biophotonic phantom.

6. The biophotonic phantom of claim 1, wherein the solid matrix of cured PDMS comprises from 0.0001% to 5% Hb by weight.

7. The biophotonic phantom of claim 1, wherein the solid matrix of cured PDMS comprises from 1.0% to 2.5% Hb by weight.

8. The biophotonic phantom of claim 1, wherein the solid matrix of cured PDMS comprises about 1.8% Hb by weight.

9. The biophotonic phantom of claim 1, wherein the Hb is oxygenated, partially oxygenated, or deoxygenated.

10. The biophotonic phantom of claim 9, wherein:
the oxygenated Hb comprises an oxygen saturation level of more than 90%;
the partially oxygenated Hb comprises an oxygen saturation level of from 10%-90%; or
the deoxygenated Hb comprises an oxygen saturation level of no less than 10%.

11. The biophotonic phantom of claim 1, wherein the solid matrix of cured PDMS comprising the distributed Hb is encased in a shell of PDMS that does not comprise Hb.

12. The biophotonic phantom of claim 1, wherein the solid matrix of cured PDMS comprising distributed Hb further comprises one or more additives comprising an optical absorber and/or an optical scatterer.

13. The biophotonic phantom of claim 1, wherein the biophotonic phantom simulates tissue with diffuse Hb distribution.

14. The biophotonic phantom of claim 13, wherein the tissue with diffuse Hb distribution is brain tissue, skin, or mucosal tissue.

15. The biophotonic phantom of claim 1, comprising a shape that simulates the morphology and optical properties of a living human organ or tissue, of body parts, or of whole animals.

16. The biophotonic phantom of claim 1, further comprising one or more embedded filaments and/or solid or hollow inclusions that provide a series of targets for calibrating or testing the performance characteristics of an optical detection system.

17. The biophotonic phantom of claim 1, wherein the solid matrix of cured PDMS comprising distributed Hb is included in the biophotonic phantom as an inclusion, and wherein the inclusion comprises an Hb concentration different from adjacent material in the biophotonic phantom.

18. A method of making a biophotonic phantom, comprising:
mixing hemoglobin (Hb) in a native conformation and uncured polydimethylsiloxane (PDMS) by sonication to form a distributed composition of the Hb in a native conformation and the PDMS; and
curing the PDMS in the composition of the Hb and PDMS using a curing agent and forming the distributed composition of Hb and PDMS into the shape of the biophotonic phantom, or a segment thereof.

19. The method of claim 18, wherein the sonication comprises, for a duration of from 8-12 hours, episodes of sonication separated by intervals that permit sufficient heat dissipation to inhibit thermal denaturation and/or oxidation of the Hb, and optionally wherein the uncured PDMS and Hb are incubated at a temperature of 0-10° C. during the sonication.

20. The method of claim 18, wherein the sonication comprises, for a duration of about 10 hours, episodes of sonication separated by intervals that permit sufficient heat dissipation to inhibit thermal denaturation and/or oxidation of the Hb, and optionally wherein the uncured PDMS and Hb are incubated at a temperature of 0-10° C. during the sonication.

21. The method of claim 18, wherein the curing the PDMS in the distributed composition of Hb and PDMS using a curing agent and forming the distributed composition of Hb and PDMS into the shape of the biophotonic phantom or segment thereof, comprises:
incubating the distributed composition of Hb and PDMS in a vacuum chamber to remove dissolved gas;
mixing the curing agent with the distributed composition of Hb and PDMS at a ratio of 1:5 to 1:15 curing agent to PDMS;
pouring the curing agent mixed with the distributed composition of Hb and PDMS into a mold; and
incubating the curing agent mixed with the distributed composition of Hb and PDMS contained in the mold at room temperature for 24 to 48 hours.

22. The method of claim 18, wherein
the sonication comprises, for a duration of about 10 hours, episodes of sonication separated by intervals that permit sufficient heat dissipation to inhibit thermal denaturation or oxidation of the hemoglobin, and optionally wherein the uncured PDMS and Hb are incubated at a temperature of 0-10° C. during the sonication; and the curing the PDMS in the distributed composition of Hb and PDMS using a curing agent and forming the distributed composition of Hb and PDMS into the shape of the biophotonic phantom, comprises:
- incubating the distributed composition of Hb and PDMS in a vacuum chamber for a duration of about 6 hours to remove dissolved gas;
- mixing the curing agent with the distributed composition of Hb and PDMS at a ratio of about 1:10 curing agent to PDMS;
- pouring the curing agent mixed with the distributed composition of Hb and PDMS into a mold; and
- incubating the curing agent mixed with the distributed composition of Hb and PDMS contained in the mold at room temperature for 24 to 48 hours.

23. The method of claim 18, further comprising adding an effective amount of a desaturation agent to the composition of Hb and PDMS to deoxygenate the Hb in the composition.

24. The method of claim 23, wherein the desaturation agent is yeast, sodium dithionite, or nitrogen gas.

25. The method of claim 18, further comprising encasing the biophotonic phantom in a shell of PDMS without hemoglobin.

26. A biophotonic phantom made by the method of claim 17.

27. A method of calibrating or testing an optical detection system, comprising:
- providing the biophotonic phantom of claim 1; and
- using the optical imaging system:
    - directing visible or near-infrared wavelengths of light to the biophotonic phantom; and
    - detecting optical and/or acoustic signals produced at the phantom responsive to the directed light.

\* \* \* \* \*